(12) United States Patent
Shemesh et al.

(10) Patent No.: US 11,950,929 B2
(45) Date of Patent: Apr. 9, 2024

(54) DISPLACEMENT SENSOR FOR USE IN MEASURING BIOLOGICAL PARAMETERS

(71) Applicant: CARDIACSENSE LTD., Caesarea (IL)

(72) Inventors: Eldad Shemesh, Binyamina (IL); Igor Kouperman, Yokneam (IL); Boris Spektor, Haifa (IL)

(73) Assignee: CARDIACSENSE LTD., Caesarea (IL)

( * ) Notice: Subject to any disclaimer, the term of this patent is extended or adjusted under 35 U.S.C. 154(b) by 689 days.

(21) Appl. No.: 17/049,744

(22) PCT Filed: May 5, 2019

(86) PCT No.: PCT/IL2019/050503
§ 371 (c)(1),
(2) Date: Oct. 22, 2020

(87) PCT Pub. No.: WO2019/215723
PCT Pub. Date: Nov. 14, 2019

(65) Prior Publication Data
US 2021/0361237 A1 Nov. 25, 2021

(30) Foreign Application Priority Data

May 10, 2018 (IL) .......................................... 259275
Aug. 29, 2018 (IL) .......................................... 261466
Dec. 26, 2018 (IL) .......................................... 263983

(51) Int. Cl.
*A61B 5/00* (2006.01)
*A61B 5/021* (2006.01)
(Continued)

(52) U.S. Cl.
CPC ........ *A61B 5/6843* (2013.01); *A61B 5/02108* (2013.01); *A61B 5/02405* (2013.01);
(Continued)

(58) Field of Classification Search
CPC .............. A61B 5/6843; A61B 5/02108; A61B 5/02405; A61B 5/02416; A61B 5/0245; A61B 5/0533; A61B 5/0816; A61B 5/14552; A61B 5/31; A61B 5/681; A61B 5/7225; A61B 2562/0233; A61B 2562/0247; A61B 5/6826; A61B 5/721; G04G 21/00–21/025
See application file for complete search history.

(56) References Cited

U.S. PATENT DOCUMENTS 8,346,328 B2 * 1/2013 Mannheimer ........ A61B 5/6843
600/310
9,874,862 B2 1/2018 Lee et al.
(Continued)

FOREIGN PATENT DOCUMENTS

CN 105286839 A 2/2016
CN 107371361 A 11/2017
(Continued)

*Primary Examiner* — Jonathan T Kuo
(74) *Attorney, Agent, or Firm* — Dorsey & Whitney LLP

(57) ABSTRACT

The present disclosure concerns a sensor assembly for measuring displacement of a contact surface at least along a central axis of the assembly caused by pressure applied on the surface by the skin of a user during measurement of at least one biological parameter of the user.

16 Claims, 16 Drawing Sheets

(51) Int. Cl.
  *A61B 5/024* (2006.01)
  *A61B 5/0245* (2006.01)
  *A61B 5/0533* (2021.01)
  *A61B 5/08* (2006.01)
  *A61B 5/1455* (2006.01)
  *A61B 5/31* (2021.01)

(52) U.S. Cl.
  CPC ........ *A61B 5/02416* (2013.01); *A61B 5/0245* (2013.01); *A61B 5/0533* (2013.01); *A61B 5/0816* (2013.01); *A61B 5/14552* (2013.01); *A61B 5/31* (2021.01); *A61B 5/681* (2013.01); *A61B 5/7225* (2013.01); *A61B 2562/0233* (2013.01); *A61B 2562/0247* (2013.01)

(56) References Cited

U.S. PATENT DOCUMENTS

| | | |
|---|---|---|
| 2007/0276270 A1 | 11/2007 | Tran |
| 2008/0071180 A1 | 3/2008 | Borgos |
| 2008/0181556 A1* | 7/2008 | Borgos ................ A61B 5/0082 385/13 |
| 2008/0183053 A1 | 7/2008 | Borgos et al. |
| 2009/0163783 A1* | 6/2009 | Mannheimer ........ A61B 5/6843 600/323 |
| 2011/0232388 A1 | 9/2011 | Butterfield |
| 2012/0215134 A1 | 8/2012 | Hunter-Jones et al. |
| 2013/0310700 A1 | 11/2013 | Wiard et al. |
| 2014/0257049 A1 | 9/2014 | Soundarapandian et al. |
| 2014/0275850 A1 | 9/2014 | Venkatraman et al. |
| 2014/0275852 A1 | 9/2014 | Hong et al. |
| 2015/0230735 A1 | 8/2015 | Venkatraman et al. |
| 2015/0261946 A1 | 9/2015 | Yoon et al. |
| 2016/0029911 A1 | 2/2016 | Lee |
| 2016/0070245 A1 | 3/2016 | Lee et al. |
| 2016/0183818 A1 | 6/2016 | Richards et al. |
| 2016/0317067 A1 | 11/2016 | Lee |
| 2017/0020399 A1 | 1/2017 | Shemesh et al. |
| 2017/0135633 A1 | 5/2017 | Connor |
| 2018/0035943 A1 | 2/2018 | Shemesh et al. |
| 2018/0146870 A1 | 5/2018 | Shemesh et al. |

FOREIGN PATENT DOCUMENTS

| | | |
|---|---|---|
| JP | 2010517617 A | 5/2010 |
| JP | 2016047092 A | 4/2016 |
| WO | 2017027551 A1 | 2/2017 |
| WO | 2018019742 A1 | 2/2018 |
| WO | 2018025199 A1 | 2/2018 |

* cited by examiner

DISPLACEMENT SENSOR FOR USE IN MEASURING BIOLOGICAL PARAMETERS

TECHNOLOGICAL FIELD

The present disclosure refers to a sensor assembly for sensing and measuring a biological parameter at a skin surface of a user.

BACKGROUND

A sensor assembly of the kind to which the present disclosure may relate is disclosed in US 2018/0035943, where the sensor assembly comprises a contact surface facing towards an exterior of the sensor assembly, a light source and a detector both facing away from the contact surface and towards a reflector configured to receive light from the light source and re-direct it to the detector. The arrangement is such that pressure applied to the contact surface causes displacement of the light source with the detector relative to the reflector, thereby changing the amount of light reaching the detector from the reflector and indicative of the displacement. In US 2018/0035943, the sensor assembly constitutes an artifact sensor in a measuring device, which comprises, in addition to the sensor assembly, one or more biological sensors fixedly associated with the contact surface of the sensor assembly and configured to optically detect one or more parameters of a pulse of the user via his skin contacted by the contact surface.

GENERAL DESCRIPTION

The present disclosure concerns a sensor assembly for measuring displacement of a contact surface at least along a central axis of the assembly caused by pressure applied on the surface by the skin of a user during measurement of at least one biological parameter of the user.

In an aspect that concerns a light-based displacement sensor, the sensor assembly operates such that the amount of light emitted from a light source directly towards a detector and detected by the detector, varies in accordance with the displacement of the contact surface caused by the pressure applied thereto. The light source and the detector are so arranged with respect to each other that light reaching the detector is mainly, or only, the one that comes directly from the light source, meaning that a minimal amount of light, if at all, reaches the detector from any elements of the sensor assembly other than the light source. The light from the light source propagates freely towards the detector in the medium between the light, e.g. air or vacuum, and not by any kind of light guide. The light source and the detector constitute a sensing unit of the assembly, which is disposed within an interior of the sensor assembly, whilst the contact surface faces towards its exterior.

The sensor assembly disclosed herein further comprises a light blocking member operative to block at least a part of light emitted by the light source towards the detector so that the light from the light source received by the light detector is indicative of the displacement of the contact surface, namely the amount of light blocked by the blocking member and is not received by the light detector is depended on the displacement of the contact surface.

In a first aspect of the present disclosure, the sensor assembly further comprises a mounting arrangement for mounting the light source and the detector of the sensing unit on two sides of the blocking member so that one of the sensing unit and the light blocking member is in fixed association with the contact surface to be movable therewith relative to the other one of the sensing unit and the light blocking member, which is free of fixed association with the contact surface.

By virtue of above arrangement, pressure applied to the contact surface causes both the contact surface and its fixedly associated member to be displaced relative to the member, which is free of such association, resulting in the light blocking member blocking at least a part of light emitted by the light source towards the detector so that the light from the light source received by the light detector is indicative of the displacement of the contact surface.

Optionally, the mounting arrangement can further comprise a flexible member, e.g. a flexible membrane, holding at least indirectly, the contact surface with the associated member so that the application of pressure to the contact surface from the exterior of the sensor assembly, causes the flexible member to flex towards the interior of the assembly, thereby displacing the contact surface and its associated member.

Further optionally, the sensor assembly can further comprise a movement blocking arrangement configured to prevent the flexible member from flexing, which if not blocked, would result in a displacement to be greater than 50, 60, 70, 80, 90, 100, 110, 120, 130, 140 or even 150 micrometer.

The mounting arrangement can comprise a contact surface holding member having the contact surface on one end thereof and the fixedly associated member mounted to the other end thereof, the contact surface holding member being movable. If the sensing unit is fixedly mounted to the contact surface holding member at its end opposite to that with the contact surface, thus being movable relative to the light blocking member, the blocking member can be fixed to a static supporting structure and vice versa.

The light blocking member can be so disposed relative to the sensing unit that their state relative to each other is changeable between a maximal blocking state, in which a maximal amount of light is blocked and a minimal amount of light reaches the detector, and a minimal blocking state, in which a minimum amount of light is blocked and a maximal amount of light reaches the detector.

In some embodiments, the range of movement of the light blocking member relative to the sensing unit can be increased by allowing the light blocking member to move into the contact surface holding member or the supporting structure.

To ensure that a minimal amount of light reaches the light detector from elements of the sensor assembly other than the light source, the detector can be provided with a field of view reducing element configured for reducing at least one of its two original fields of view in two mutually perpendicular planes both comprising an optical axis of the sensing unit. When one of the planes is parallel to a plane, to which the sensing unit is mounted, the field of view reducing element can be configured to reduce the field of view of the detector in that plane, while maintaining the original field of view in the plane perpendicular thereto, and vice versa. The plane to which the sensing unit is mounted can be perpendicular to the central axis of the assembly.

To ensure that light from the light source is emitted directly to the detector and a minimal amount of light reaches elements other than the detector, from which it can be reflected towards the detector, the light source can be provided with a divergence angle reducing element configured to reduce the divergence angle of the light source in one of two mutually perpendicular planes both comprising the optical axis of the sensing unit. When one of the two planes is parallel to a plane to which the sensing unit is mounted, the divergence angle reducing element can be configured to reduce the divergence angle in that plane, while maintaining its original divergence angle in the plane perpendicular thereto, and vice versa.

In accordance with a second aspect of the present disclosure, the optical axis of the sensing unit lies in a plane perpendicular to the axis of movement of the contact surface, the light source being configured to emit light along the optical axis to the light detector facing towards the light source, the light blocking mechanism being operative to change the amount of light reaching the detector directly from the light source in consequence with displacement of the contact surface caused by pressure applied thereto by the skin of a user.

According to this aspect, light along the optical axis, if not blocked, propagates from the light source directly to the detector, has a length which is defined by a distance between the light source and the detector, and which is invariant during the operation of the sensor assembly.

Features of the sensor assembly according to the first aspect of the present disclosure can be used in that of the second aspect and vice versa, and any one or more of the following additional features can also be used in both of them:
- the light source can comprise one or more light source elements;
- the light source can comprise at least one Light-Emitting Diode (LED);
- the light detector can comprise at least one photodiode (PD);

The sensor assembly of each one of the above aspects allows sensing of very small displacements of its contact surface caused by pressure externally exerted thereon, by the skin of a user during measurements of at least one biological parameter thereat. For example, the measured displacements can be in the range of 0.1-100 micrometer and the pressure can be in the range of 0-40 mm Hg.

A further aspect of the present disclosure concerns a measurement device comprising a biological sensor for performing measurements of at least one biological parameter at the skin of a user, and a sensor assembly of the kind described above, for identifying artifacts in measurements of the biological parameter/s. The measurement device can be configured so that the biological sensor and the contact surface face in the same direction and are disposed so as to make sure that they both can simultaneously be in contact with the measurement skin of user, or in some embodiments the biological sensor is at least in the vicinity thereof. In some embodiments the biological sensor can be accommodated or embedded within the contact surface of the pressure/displacement sensor assembly.

The biological sensor can include at least one light source such as a LED and at least one light detector such as a PD. The biological parameter can be, for example, a heart rate and/or a heart rate variability. In some embodiments, the biological sensor is a PPG sensor. In a specific embodiment the PPG sensor can comprise or be associated with an ECG electrode(s).

The measuring device can further comprise a control unit that is in data communication with the sensing unit of the displacement sensor assembly. The control unit can comprise an analyzer configured to analyze data received from the detector of the sensing unit and identify artifacts caused by movement of the measurement surface.

The measuring device can be in the form of a wrist watch, whose contact surface is configured to contact the wrist of a user, wearing the wrist watch. The wrist watch can further comprise an output module configured to communicate the artifacts identified by the analyzer of the control unit to a processing unit or to a communication center.

In some embodiments the biological sensor is configured to perform measurements that can be outputted as at least one of Electroencephalogram (EEG), Electrocardiography (ECG) and photoplethysmograph (PPG).

Sensing displacement of a contact surface upon pressure applied thereto by a subject's skin, as in the sensor assembly disclosed herein, can be used in a method for measuring a biological parameter in the subject.

Thus, in accordance with another aspect of the present disclosure there is provided a method for measuring a biological parameter of a subject. The method comprises contacting a contact surface of a displacement sensor with a skin surface of the subject and collecting data indicative of movement of the contact surface, this data being associated with the pressure applied by the skin on the displacement sensor.

The method includes emitting light from a light source in the direction of a light detector along an optical axis and permitting a light blocking member to block light emitted by the light source in a manner proportional to the displacement of the contact surface. The method further comprises obtaining data indicative of light intensity detected by the light sensor and determining displacement of the contact surface based thereon.

In some embodiments, the movement of the skin, and thus the pressure applied onto the displacement sensor, occurs due to expansion and narrowing of blood vessels. In other words, the blood vessels expand when blood reaches thereto from the heart and narrow when blood goes back to the heart. The expansion or narrowing of the blood vessels causes the movement of the skin surface against the displacement sensor, and pressure applied onto the displacement sensor is detected. The data indicative of movement of the skin surface is collected. The collected data can then be processed to provide therefrom one or more biological parameters.

The biological parameter may be any parameter that is associated directly or indirectly with the expansion or narrowing of the blood vessels.

In some embodiments, the biological parameter comprises blood pressure.

In some embodiments, the biological parameter comprises heart rate.

In some embodiments, the biological parameter comprises respiration rate.

In some embodiments, the biological parameter comprises oxygen saturation.

In some embodiments, the method comprises contacting the skin surface with a contact surface of a displacement sensor.

In some embodiments, the method comprises fixedly mounting the displacement sensor onto the skin such that there is a fixed contact between the contact surface of the displacement sensor and the surface of the skin.

In some embodiments, the fixation of the displacement sensor is such that the contact surface thereof is mounted over the artery. Fixation of the contact surface over the artery may increase accuracy of measurement.

In some embodiments, the displacement sensor is placed over the radial artery.

In some embodiments, the method comprises emitting light towards a detector within the displacement sensor and collecting signals indicative of the amount of light received by the detector, said signals being indicative of the displacement of the contact surface with respect to movement of said skin surface.

The method may comprise a continuous detection, yet in some embodiments, the detection is periodically, i.e. during pre-set time windows. A time window may be several seconds, e.g. 5, 10 or 20 seconds, and up to 60, 90 or 120 seconds.

The signal data is then processed. In some embodiments, the method comprises processing the signal data collected with respect to the amount of light received by the detector.

In some embodiment, the collected signal data is processed with a pulse pressure analysis model. In some embodiments, the pulse pressure analysis comprises pulse decomposition analysis.

In some embodiment, the collected signal data is processed with a wave analysis model.

In some embodiments, the signal data is processed by a combination of analysis techniques.

The signal obtained by the displacement sensor may have two components, an AC component and a DC component. The AC component of the signal may comprise many frequencies, each may represent or being indicative of a biological parameter. The DC component of the signal may, among other, being indicative of respiration rate of the subject. Thus, by extracting the values of the DC component of the signal, the respiration rate of the subject may be determined. In some embodiments, the values of the AC signal (e.g. amplitude) are extracted and processed together with the DC component values to obtain the respiration rate of the subject. The use of the two components may increase the accuracy of the measurement of the biological parameter, e.g. respiration rate.

In some embodiments, the displacement sensor is one of the kind used in the sensor assembly disclosed herein. According to this embodiment, the method comprises fixedly mounting the sensor assembly disclosed herein on the skin surface of a subject.

Also disclosed herein is a system for determining a biological parameter of a subject. The system comprising: (a) a displacement sensor for generating data indicative of movement of a subject's skin surface, and (b) a control unit in data communication with the displacement sensor for receiving therefrom collected data and extracting a biological parameter from the collected data.

The displacement sensor comprises a contact surface, a sensing unit and a light blocking member.

The sensing unit having a light detector and a light source with an optical axis defined between them, the light source being configured to emit light directly toward the sensor which is configured to detect the light.

The light blocking member associated with the sensing unit, such that displacement of the contact surface induces the blocking member to block light propagating along said axis in a manner proportional to the displacement of the contact surface.

In some embodiments, the displacement sensor is of the kind described here, i.e. that comprises (i) a contact surface configured to contact skin surface of the subject; (ii) a sensing unit comprising at least one detector and at least one light source configured to emit light directly towards the detector; and (iii) a light blocking member associated with the sensing unit.

The light emitted from the light source and received by the light detector is indicative of the displacement of the contact surface with respect to movement of the skin surface.

In some embodiments, the control unit comprises extractor module for extracting the biological parameter from the collected data. As described above, the biological parameter may be any one or combination of blood pressure, heart rate or respiration rate, each constituting a separate embodiment of the present disclosure.

The extractor module may be configured to extract the biological parameters by any one or combination of (i) applying pulse pressure wave analysis models, (ii) identifying the DC component of the collected data; and (iii) applying a signal filter.

In some embodiments, the system may also comprise a fixation element for maintaining the displacement sensor in position so as to have a better control of the place where the measurement is taken. For example, the displacement sensor may be fixed to the skin surface by a wristband or a clip held by a wristband.

In some embodiments, the system comprises more than one displacement sensors to mutually detect different signals and extract therefrom the one or more biological parameters.

In some embodiments, at least one of the displacement sensors, when more than one is used, is in data communication with an optical biological sensor, such as a PPG sensor, and having a common sensing surface therewith. Such displacement sensor may be configured to provide optically sensed data indicative of the movement of the common sensing surface. In this manner, an increase in the accuracy of the measurements of the biological sensor may be achieved by providing a relevant data of the movement of the skin surface. This data may comprise artifact signals that may be sensed by the biological sensor and therefore the eventual parameter sensed by the biological sensor may be determined while considering the artifact signals.

The other displacement sensor may be fixed at a different location to collect data indicative of other biological parameters or for a dual measurement of the same biological parameter for increasing the accuracy of the measurement. For example, while one displacement sensor may be placed within a main body of a wrist watch, the other displacement sensor may be located within a band linked to the wrist watch.

The above described system may be comprised in a measuring device.

In some embodiments, wherein the measuring device comprising two displacement sensors, the first sensor is comprised within a main body of the measuring device and the second sensor is comprised within a band linked to the measuring device.

In some embodiments, the measuring device comprising an electric-based biological sensor formed on a main body thereof.

In some embodiments, the measuring device is configured as a wrist watch.

In some other embodiments, the measuring device is in the form of a ring-shaped element configured to be worn on a finger of a subject.

Yet another aspect of the present disclosure provides a Hall-effect based displacement sensor for determining movement of a skin contact surface. The displacement sensor includes a housing structure and a skin contact surface displaceable with respect to the housing along a central axis normal to a plane spanned by the skin contact surface. Therefore, while the housing and components fixedly attached thereto remain stationary, the contact surface is configured for displacement at least along the central axis. The displaceable sensor further includes one or more sensing units, each of which comprising a Hall-effect sensor pair. Each of the Hall-effect sensor pairs comprises a displaceable member that is displaceable together with the contact surface, and a stationary member of the that is in a fixed position with respect to the housing. The Hall-effect sensor pair is configured to obtain Hall-effect measurement data that is indicative of the movement of the skin contact surface.

The displacement sensor may include two or more sensing units such that the Hall-effect measurement data of each sensing unit is indicative of the movement of a different portion of the skin contact surface. In this manner, the displacement sensor can sense the inclination of the contact surface with respect to a steady state where no pressure applied thereon. For example, when the pressure applied on the contact surface is varied over different portions of the contact surface, each portion is displaced according to the pressure applied thereon and each Hall-effect sensor pair is configured to sense the displacement of each portion independently. According to the above, the Hall-effect measurement data that is obtained from two or more sensing units may be indicative of a roll or a tilt of the skin contact surface.

In some embodiments, the displaceable sensor comprises a flexible member that links the contact surface to the housing to allow the displacement thereof. In some embodiments, the flexible member links the displaceable plate to the housing. The flexible member permits the contact surface to roll and tilt with respect to at least one axis, namely allowing a 3-dimensional movement.

In some embodiments, the displaceable member of the Hall-effect sensor pair is being a constant magnet, and the stationary member is being a Hall-effect sensor. However, in some embodiments, the displaceable member is being a Hall-effect sensor and the stationary member is being a constant magnet. The Hall-effect measurement data that is generated by each Hall-effect sensor pair may include a voltage measurement data, wherein the value of the voltage is indicative of the displacement of the contact surface.

Another aspect of the present disclosure provides a measurement device that comprises the Hall-effect based displacement sensor.

In some embodiments of the measurement device, the skin contact surface is configured to be brought into contact with a skin surface in a vicinity of an artery of a subject, and the Hall-effect measurement data is indicative of blood pressure of the subject.

In some embodiments, the measurement device further comprising a control unit and at least one biological sensor configured to provide biological sensing data, e.g. optical measurements of the blood or electrical measurements of heart activity. The control unit is configured to receive the Hall-effect measurement data and the biological sensing data, process them and extract a biological parameter based on a relation between the Hall-effect measurement data and the biological sensing data.

In some embodiments of the measurement device, the at least one biological sensor is disposed between the displaceable member and the skin contact surface and is displaceable together with the displaceable member and the contact surface. In some embodiments, the biological sensor is further configured to obtain the biological sensing data through the contact surface. For example, the biological sensor may be an optical sensor that optically measures blood response through the skin contact surface and the skin of the subject. In some embodiments, the biological sensor may be an electrical sensor.

In some embodiments of the measurement device, the optical sensor is being a PPG sensor and the electrical sensor is being an ECG sensor.

The displacement sensor may be configured to determine artifact effects that are considered as noise in measurements of biological parameters on or through the skin surface of a subject, such as movements of the skin that results from fingers movements. Therefore, the Hall-effect measurement data may comprise artifact data that is indicative of such artifact effects. The control is configured to identify the artifact data and extract the biological parameter from the biological sensing data by taking into account the artifact data.

In some embodiments of the measurement device, one member of the Hall-effect sensor pair is integrated into a PCB of the measurement device, e.g. the motherboard of the device. This permits to minimize the space that is required for the displacement sensor.

Yet another aspect of the present disclosure provides, a method for measuring a biological parameter of a subject. The method includes: (a) contacting a skin contact surface of a displacement sensor with a skin surface of the subject; (b) obtaining data indicative of displacement of the contact surface; (c) processing the data to provide the biological parameter. The data indicative of a displacement of the contact surface is obtained by (i) applying a magnetic field on a Hall-effect sensor, wherein the magnitude of the magnetic field is proportional to the displacement of the contact surface, and (ii) obtaining Hall-effect measurement data indicative of voltage detected in the Hall-effect sensor and determining displacement of the contact surface based thereon.

In some embodiments, the method further comprising making use of a displacement sensor that comprises a housing, a skin contact surface and a sensing unit having at least one Hall-effect sensor pair. The Hall-effect sensor pair includes a displaceable member that is displaceable together with the contact surface and a stationary member that is in a fixed position with respect to the housing. A Hall-effect measurement data that is obtained by the Hall-effect sensor is indicative of the movement of the skin contact surface.

In some embodiments of the method, the displacement sensor is that of any of the above-described embodiments of the Hall-effect based displacement sensor.

In some embodiments of the method, the biological parameter comprises blood pressure, heart rate, oxygen saturation or respiration rate.

In some embodiments of the method, the contacting comprises holding said displacement sensor in proximity with an artery.

In some embodiments of the method, the contacting comprises holding the displacement sensor over an artery.

In some embodiments of the method, the processing comprises at least one of pulse pressure analysis model and wave analysis model.

In some embodiments of the method, the pulse pressure analysis comprises pulse decomposition analysis.

In some embodiments of the method, the processing comprises extracting the DC component from the data or applying a signal filter.

The following are various embodiments of different aspects of the present disclosure:

Embodiments

1. A displacement sensor assembly configured for use in measuring a biological parameter at the skin of a user, the assembly comprising:

a contact surface facing towards an exterior of the assembly and configured to be brought into at least an indirect contact with the skin of a user, the contact surface being movable along a central axis of the assembly when pressure is applied thereto from the exterior of the assembly;

a sensing unit having an optical axis and comprising at least one detector and at least one light source configured to emit light along the optical axis directly towards the detector, namely the light propagates through a space, e.g. air or vacuum;

a light blocking member associated with the sensing unit; and a mounting arrangement, by virtue of which the sensing unit and the blocking member are mounted within an interior of the assembly so that one of these members is fixedly associated with the contact surface so as to be movable therewith, and the other one of these members is free of such fixed association with the contact surface, the arrangement being such that movement of the member associated with the contact surface relative to the member, which is free of such association, is configured to cause the light blocking member to at least partially block light emitted by the light source towards the detector, allowing that light from the light source received by the light detector to be indicative of the displacement of the contact surface.

2. The sensor assembly of embodiment 1, wherein the mounting arrangement comprises at least one flexible member, to which the contact surface and the member fixedly associated therewith are connected at least indirectly, said member being configured to flex when pressure is applied to the contact surface, thus allowing the contact surface and the member fixedly associated therewith to move relative to the member, which is free of such association.

3. The sensor assembly of embodiment 1 or 2, wherein said mounting arrangement comprises a contact surface holding member having the contact surface at its distal end and a base surface at its proximal end, to which said the member associated with the contact surface is fixedly mounted.

4. The sensor assembly of embodiment 3 when dependent on embodiment 2, wherein said contact surface holding member is mounted to said flexible member so as to be moved thereby when pressure is applied to the contact surface from the exterior of the assembly.

5. The sensor assembly of embodiment 3 or 4, wherein the central axis of the assembly constitutes an axis of symmetry of said flexible member and said contact surface holding member.

6. The sensor assembly of any one of embodiments 3, 4 or 5, wherein the optical axis of the sensing unit lies in a plane which is perpendicular to the central axis of the assembly.

7. The sensor assembly of any one of embodiments 3 to 6, wherein the base surface is perpendicular to the central axis of the assembly.

8. The sensor assembly of any one of embodiments 1 to 7, wherein the light source has original divergence angles in two mutually perpendicular planes both comprising the optical axis, one of the planes being perpendicular to the central axis of the assembly, and wherein the light source is provided with a divergence angle reducing element configured for reducing at least one of the divergence angles of the light source.

9. The sensor assembly of embodiment 8, wherein the divergence angle reducing element is configured to reduce the divergence angle of the light source in the plane perpendicular to the central axis of the assembly, while maintaining its original divergence angle in the plane perpendicular thereto.

10. The sensor assembly according to any one of embodiments 1 to 9, wherein the detector has original fields of view in two mutually perpendicular planes both comprising the optical axis, one of the planes being perpendicular to the central axis of the assembly, and wherein the detector is provided with a field of view reducing element configured for reducing at least one of the fields of view of the detector, optionally, in the plane perpendicular to the central axis of the assembly, such that at least most of the light received thereby is the light emitted from the light source towards the detector.

11. The sensor assembly of embodiment 10, wherein the field of view reducing element is configured to reduce the field of view of the detector in the plane perpendicular to the central axis of the assembly, while maintaining its original field of view in the plane perpendicular thereto.

12. The sensor assembly of any one of embodiments 1 to 11, wherein said pressure is in the range of 0-40 mm Hg.

13. The sensor assembly of embodiment 2 and any one of embodiments 3 to 12, when dependent at least indirectly on embodiment 2, further comprising a movement blocking arrangement configured to prevent the flexible member from flexing, which if not blocked, could result in the displacement of greater than 1 mm of the member associated with the contact surface.

14. The sensor assembly of any one of embodiments 1 to 13, wherein the light source comprises at least one Light-Emitting Diode (LED).

15. The sensor assembly of any one of embodiments 1 to 14, wherein the light detector comprises at least one photosensitive element, optionally, a photodiode (PD).

16. The sensor assembly of any one of embodiments 1 to 15, wherein the member, which is free of fixed association with the contact surface, is maintained static at least during the movement of the contact surface and its associated member.

17. The sensor assembly of any one of embodiments 1 to 16, wherein during the movement of the contact surface with its fixedly associated member, the sensing and light blocking members change their state relative to each other between a minimal blocking state, in which the light blocking member blocks a minimal amount of light emitted by the light source towards the detector, and a maximal blocking state in which the light blocking member blocks a maximal amount of light emitted by the light source towards the detector.

18. The sensor assembly of embodiment 17, wherein the light blocking member has an edge, which is closer to the contact surface than a remainder of the light blocking member and which is configured to take, during the movement of the contact surface with its fixedly associated member, a plurality of positions relative to the contact surface between a maximally spaced position in the minimal blocking state, and a minimally spaced position in the maximal blocking state.

19. The sensor assembly of embodiment 3 or any one of embodiments 4 to 18 when dependent at least indirectly on embodiment 3, wherein the contact surface holding member is configured to receive therein through the base surface at least a portion of the light blocking member in at least one of the maximal and minimal blocking states of the sensor assembly.

20. The sensor assembly of embodiment 19 when dependent on embodiment 18, wherein said portion of the light blocking member comprises its said edge.

21. A displacement sensor assembly configured for use in measuring a biological parameter at the skin of a user, the assembly comprising
    a contact surface facing towards an exterior of the assembly and configured to be brought into at least an indirect contact with the skin of a user, the contact surface being movable along a central axis of the assembly when pressure is applied thereto by the skin of a user;
    a sensing unit disposed within an interior of the assembly and having an optical axis lying in a plane perpendicular to the central axis of the assembly; the sensing unit comprising a light source configured to emit light along the optical axis and a light detector facing towards the light source and configured to detect light emitted by the light source directly towards the detector, namely the light emitted from the light source propagates through space, e.g. air or vacuum and detected by the detector; and
    a light blocking member operative to change the amount of light reaching the detector directly from the light source in consequence with displacement of the contact surface caused by pressure applied thereto by the skin of a user.

22. The sensor assembly of embodiment 21, further comprising a contact surface holding member having a central axis perpendicular to the contact surface, the contact surface holding member being movable along said central axis when pressure is applied to the contact surface from the exterior of the assembly.

23. The sensor assembly of embodiment 22, wherein the contact surface holding member has the contact surface at its distal end and a base surface at its proximal end spaced from the distal end along the central axis, and the assembly further comprises a static supporting structure, and wherein one of the sensing unit and the light blocking member is fixedly mounted to the base surface and is thus movable together with the contact surface holding member, and the other of these members is fixedly mounted to the static supporting structure.

24. The sensor assembly of embodiment 23, wherein the base surface is perpendicular to the central axis of the assembly and the sensing unit is fixedly mounted thereto.

25. The sensor assembly of any one of embodiments 21 to 24, wherein the light source has original divergence angles in two mutually perpendicular planes both comprising the optical axis, one of the planes being perpendicular to the central axis of the assembly, and wherein the light source is provided with a divergence angle reducing element configured for reducing at least one of the divergence angles of the light source.

26. The sensor assembly of embodiment 25, wherein the divergence angle reducing element is configured to reduce the divergence angle of the light source in the plane perpendicular to the central axis of the assembly, while maintaining its original divergence angle in the plane perpendicular thereto.

27. The sensor assembly according to any one of embodiments 21 to 26, wherein the detector has original fields of view in two mutually perpendicular planes both comprising the optical axis, one of the planes being perpendicular to the central axis of the assembly, and wherein the detector is provided with a field of view reducing element configured for reducing at least one of the fields of view of the detector, optionally, in the plane perpendicular to the central axis of the assembly, such that at least most of the light received thereby is the light emitted from the light source towards the detector.

28. The sensor assembly of embodiment 27, wherein the field of view reducing element is configured to reduce the field of view of the detector in the plane perpendicular to the central axis of the assembly, while maintaining its original field of view in the plane perpendicular thereto.

29. The sensor assembly of any one of embodiments 1 to 28, constituting an artifact sensor assembly in a measuring device comprising, in addition thereto, at least one biological sensor configured to measure at least one biological parameter 30. A measuring device comprising at least one biological sensor and further comprising a sensor assembly according to any one of embodiments 1 to 29, configured to increase accuracy of operation of the biological sensor, the biological sensor being configured for optically measuring at least one biological parameter of a user, optionally at least one of a heart rate and heart rate variability.

31. The measuring device of embodiment 30, being in the form of a wrist watch.

32. The measuring device of embodiment 29 or 30, wherein the biological sensor faces in the same direction as the contact surface.

33. The measuring device of embodiment 32, wherein the biological sensor is fixed to the contact surface.

34. The measuring device of embodiment 32, wherein the contact surface constitutes a part of a structure, which holds the at least one biological sensor.

35. The measuring device of any one of embodiments 30 to 34, comprising a control unit in data communication with the detector of the sensor assembly, said control unit comprising
    an analyzer configured to analyze the data received from the detector and generate data indicative of displacement of the contact surface; and
    an output module for communicating said data.

36. The measuring device of any one of embodiments 30 to 35, wherein the biological sensor is one of Electroencephalogram (EEG), Electrocardiography (ECG), photoplethysmograph (PPG), and Galvanic Skin Response (GSR).

37. A method for measuring a biological parameter of a subject, the method comprising
    contacting a contact surface of a displacement sensor with a skin surface of the subject;
    obtaining data indicative of displacement of the contact surface; and
    processing said data to provide said biological parameter;
    wherein the method comprises
    emitting light from a light source in the direction of a light detector along an optical axis permitting a light blocking member to block light emitted by the light source in a manner proportional to the displacement of the contact surface, and comprises
obtaining data indicative of light intensity detected by the light sensor and
determining displacement of the contact surface based thereon.

38. The method of embodiment 37, comprising making use of a displacement sensor comprises:
a contact surface;
a sensing unit having at least one light detector and at least one light source with an optical axis defined between them, the light source being configured to emit light toward the sensor which is configured to detect the light; and
a light blocking member associated with the sensing unit, such that displacement of the contact surface induces the blocking member to block light propagating along said axis in a manner proportional to the displacement of the contact surface.

39. The method of embodiment 38, wherein the displacement sensor is that of any one of embodiments 1-29.

40. The method of embodiment 38 or 39, wherein the biological parameter comprises blood pressure, heart rate, oxygen saturation or respiration rate.

41. The method of any one of embodiments 38 to 40, wherein said contacting comprises holding said displacement sensor in proximity with an artery.

42. The method of embodiment 41, wherein said contacting comprises holding the displacement sensor over an artery.

43. The method of any one of embodiments 38 to 42, wherein said processing comprises at least one of pulse pressure analysis model and wave analysis model.

44. The method of embodiment 43, wherein said pulse pressure analysis comprises pulse decomposition analysis.

45. The method of any one of embodiments 37 to 44, wherein said processing comprises extracting the DC component from the data or applying a signal filter.

46. A system for determining a biological parameter of a subject, the system comprising:
(i) displacement sensor comprising
a contact surface configured to contact skin surface of the subject;
a sensing unit having at least one light detector and at least one light source with an optical axis defined between them, the light source being configured to emit light directly toward the sensor which is configured to detect the light; and
a light blocking member associated with the sensing unit, such that displacement of the contact surface induces the blocking member to block light propagating along said axis in a manner proportional to the displacement of the contact surface to obtain data indicative of displacement of the contact surface;
(ii) a control unit in data communication with the displacement sensor for receiving data indicative of said movement of the contact surface;
said control unit comprises extractor module for extracting the biological parameter from the data indicative of movement of a skin surface.

47. The system of embodiment 46, wherein the displacement sensor is any one of embodiments 1-29.

48. The system of embodiment 46 or 47, further comprising a fixation element for holding the displacement sensor in contact with the skin surface.

49. The system of any one of embodiments 46 to 48, wherein the biological parameter comprises blood pressure, heart rate, oxygen saturation or respiration rate.

50. The system of any one of embodiments 46 to 49, wherein the extractor configured and operable for at least one of (i) applying at least one of pulse pressure wave analysis models, (ii) identifying the DC component of the data; and (iii) applying a signal filter.

51. The system of any one of embodiments 46 to 50, comprising an optical biological sensor having a common contact surface with the displacement sensor.

52. The system of any one of embodiments 46 to 51, comprising an electric-based biological sensor that comprises a sensing surface continuously surrounding the contact surface of the displacement sensor.

53. The system of any one of embodiments 46 to 52, comprising a first displacement sensor and a second displacement sensor, at least one of the first and second displacement sensors is in data communication with an optical biological sensor and having a common contact surface therewith, and being configured for providing said optical biological sensor data indicative of the movement of the common sensing surface.

54. A measuring device comprising the system of embodiments 46 to 53.

55. A measuring device comprising the system of embodiment 54, wherein the first sensor is comprised within a main body of the measuring device and the second sensor is comprised within a band linked to the measuring device.

56. The measuring device of embodiment 54 or 55, comprising an electric-based biological sensor formed on a main body of the measuring device.

57. The measuring device of any one of embodiments 54 to 56, wherein the measuring device is configured as a wrist watch.

58. The measuring device of any one of embodiments 54 to 56, wherein the measuring device is in the form of a ring-shaped element configured to be worn on a finger of a subject.

59. A displacement sensor for determining movement of a skin contact surface, comprising:
a housing;
a skin contact surface displaceable with respect to the housing along a central axis normal to said surface;
one or more sensing units, each of which comprising a Hall-effect sensor pair, wherein
a displaceable member of the pair being displaceable together with the contact surface, and
a stationary member of the pair being in a fixed position with respect to the housing;
whereby a Hall-effect measurement data of the Hall-effect sensor is indicative of the movement of the skin contact surface.

60. The displacement sensor of embodiment 59, comprising two or more sensing units, the Hall-effect measurement data of each sensing unit is indicative of the movement of different portion of the skin contact surface.

61. The displacement sensor of embodiment 59 or 60, comprising a displaceable plate displaceable with the skin contact surface, the displaceable plate comprises the displaceable member of one or more sensing units.

62. The displacement sensor of embodiment 60 or 61, wherein Hall-effect measurement data of the two or more sensing units is indicative of at least one of a tilt and roll of the skin contact surface with respect to a non-displaced state.

63. The displacement sensor of any one of embodiments 59-62, wherein the contact surface is configured to move with respect to at least one more axis, other than the central axis.

64. The displacement sensor of any one of embodiments 59-63, wherein one of the Hall-effect sensor pair is configured as a constant magnet.

65. The displacement sensor of any one of embodiments 59-64, wherein the Hall-effect measurement data comprises a voltage measurement data, the value of the voltage is indicative of the displacement of the contact surface.

66. A measurement device comprising the displacement sensor of any one of embodiments 59-65.

67. The measurement device of embodiment 66, wherein the skin contact surface is configured to be brought into contact with a skin surface in a vicinity of an artery of a subject, and the Hall-effect measurement data is indicative of blood pressure of the subject.

68. The measurement device of embodiment 67, comprising
at least one biological sensor configured to provide biological sensing data;
a control unit configured to receive the Hall-effect measurement data and the biological sensing data and extract a biological parameter based on a relation between the Hall-effect measurement data and the biological sensing data.

69. The measurement device of embodiment 68, wherein the at least one biological sensor is disposed between the displaceable member and the skin contact surface, and configured to move together with the displaceable member.

70. The measurement device of embodiment 69, wherein the biological sensor is selected from an optical sensor and an electrical sensor.

71. The measurement device of embodiment 70, wherein the optical sensor being a PPG sensor and the electrical sensor being an ECG sensor.

72. The measurement device of any one of embodiments 68-71, wherein the Hall-effect measurement data comprises artifact data indicative of artifact effects.

73. The measurement device of embodiment 72, wherein the control unit is configured to identify the artifact data, and extract the biological parameter by reducing the artifact data from the biological sensing data.

74. The measurement device of any one of embodiments 66-73, wherein one member of the Hall-effect sensor pair is integrated into a PCB of the measurement device.

75. A method for measuring a biological parameter of a subject, the method comprising
contacting a skin contact surface of a displacement sensor with a skin surface of the subject;
obtaining data indicative of displacement of the contact surface; and
processing said data to provide said biological parameter;
wherein the method comprises
applying magnetic field on a Hall-effect sensor, wherein the magnitude of the magnetic field is proportional to the displacement of the contact surface, and
obtaining Hall-effect measurement data indicative of voltage detected in the Hall-effect sensor and determining displacement of the contact surface based thereon.

76. The method of embodiment 75, comprising making use of a displacement sensor comprises:
a housing;
a skin contact surface;
a sensing unit having at least one Hall-effect sensor pair wherein
a displaceable member of the pair being displaceable together with the contact surface, and
a stationary member of the pair being in a fixed position with respect to the housing;
whereby a Hall-effect measurement data of the Hall-effect sensor is indicative of the movement of the skin contact surface.

77. The method of embodiment 76, wherein the displacement sensor is that of any one of embodiments 59-65.

78. The method of any one of embodiments 75 to 77, wherein the biological parameter comprises blood pressure, heart rate, oxygen saturation or respiration rate.

79. The method of any one of embodiments 75 to 78, wherein said contacting comprises holding said displacement sensor in proximity with an artery.

80. The method of embodiment 79, wherein said contacting comprises holding the displacement sensor over an artery.

81. The method of any one of embodiments 75 to 80, wherein said processing comprises at least one of pulse pressure analysis model and wave analysis model.

82. The method of embodiment 81, wherein said pulse pressure analysis comprises pulse decomposition analysis.

83. The method of any one of embodiments 75 to 82, wherein said processing comprises extracting the DC component from the data or applying a signal filter.

BRIEF DESCRIPTION OF THE DRAWINGS

In order to better understand the subject matter that is disclosed herein and to exemplify how it may be carried out in practice, embodiments will now be described, by way of non-limiting examples only, with reference to the accompanying drawings, in which:

FIG. 9A shows the clip as a whole; FIG. 9B shows the interior elements of the clip;

DETAILED DESCRIPTION OF EMBODIMENTS

Figure 1A:
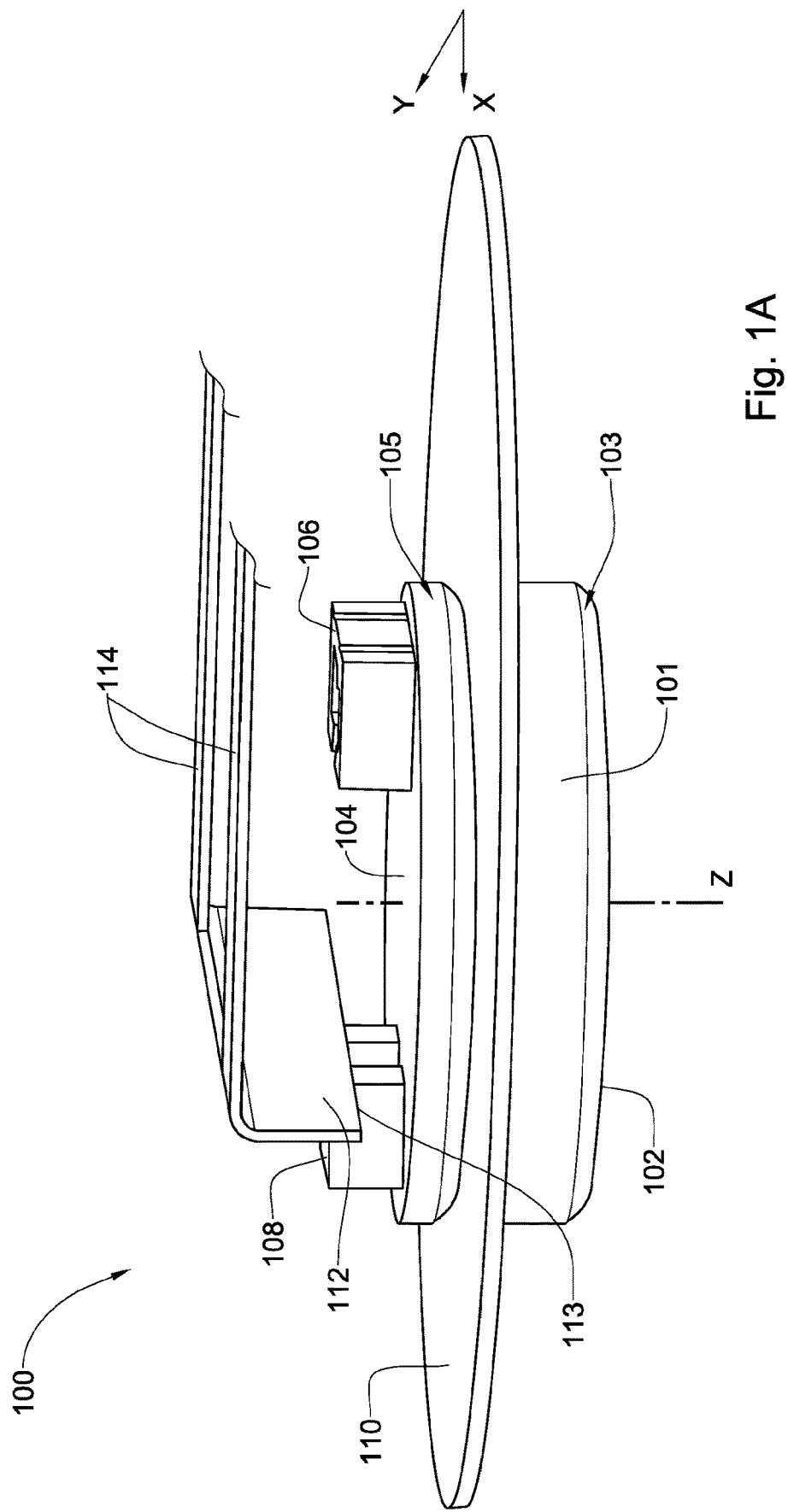
FIG. 1A is an isomeric side view of a sensor assembly according to an example of one aspect of the present disclosure.
Figure 1B:
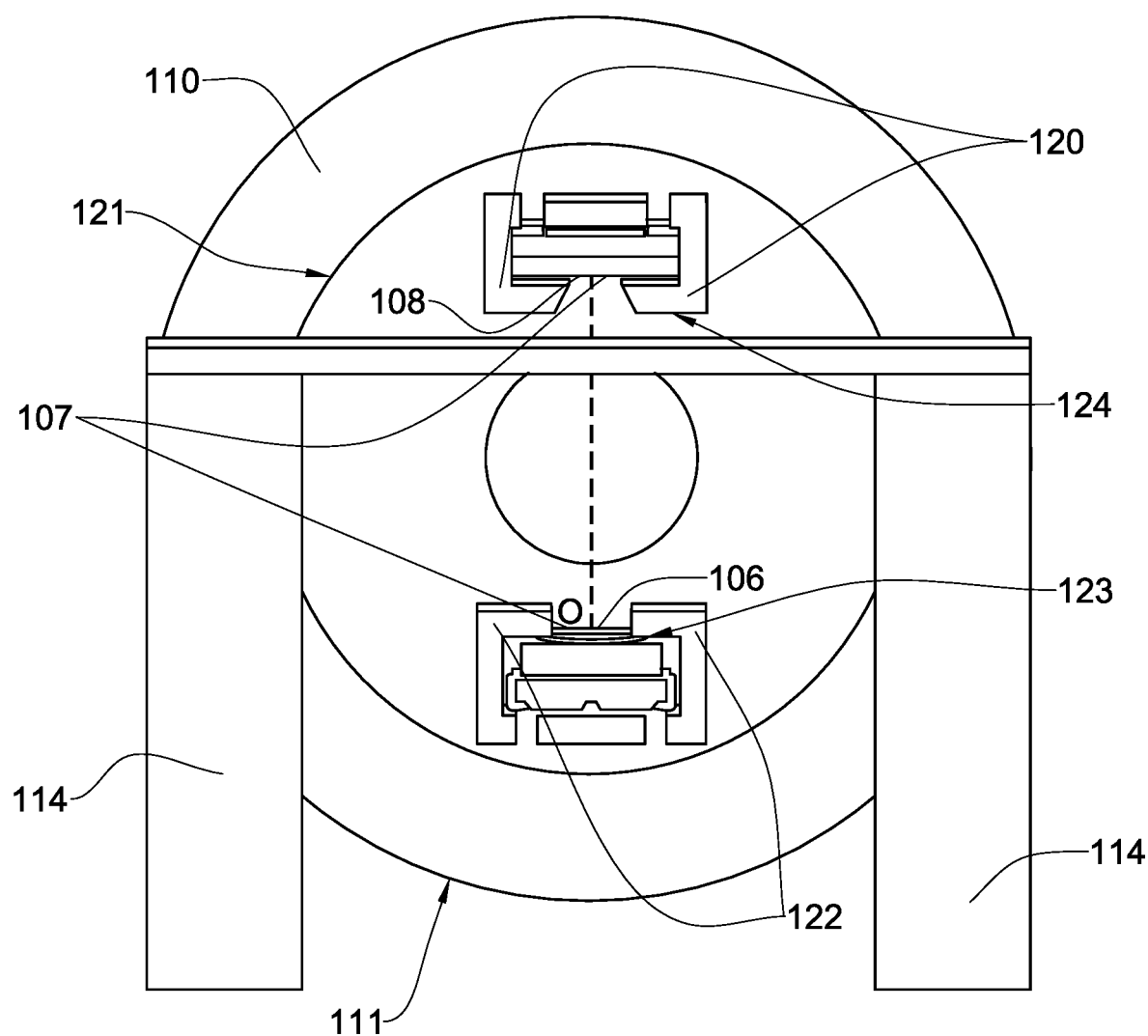
FIG. 1B is a schematic top view of the sensor assembly shown in FIG. 1B.
Figure 1C:
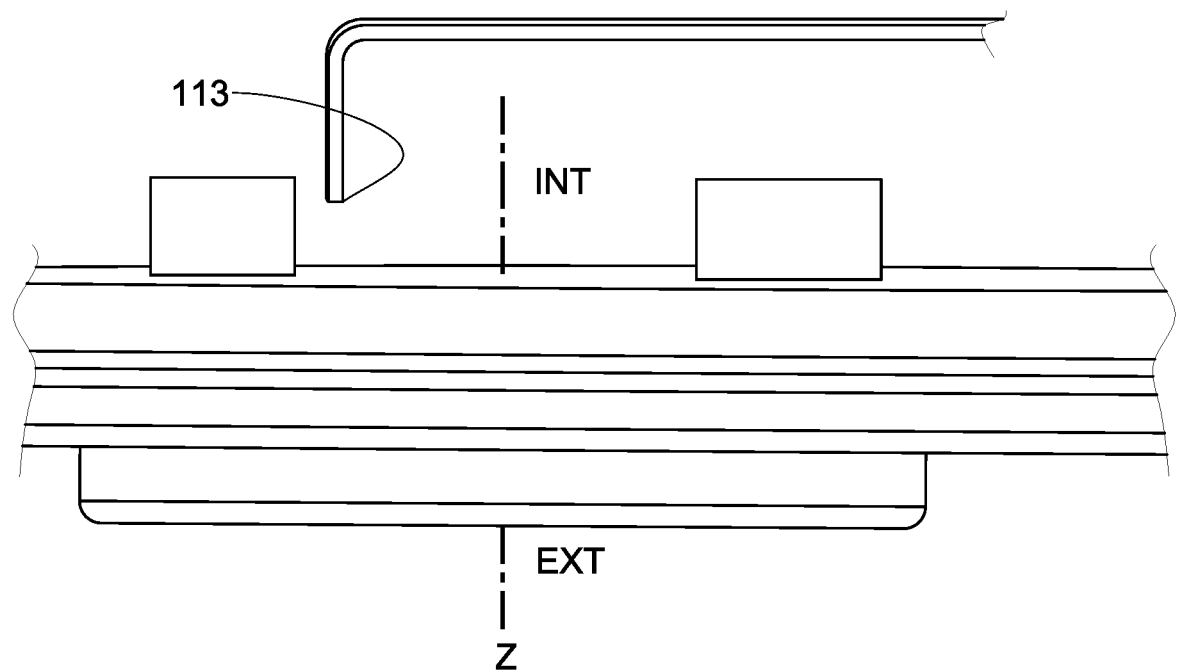
FIG. 1C is a schematic side view of the sensor assembly shown in FIGS. 1A and 1B.

FIGS. 1A to 1C illustrate one example of a sensor assembly configured for measuring displacements of its contact surface along a central axis Z of the assembly, caused by pressure externally exerted thereon, by the skin of a user during measurements of at least one biological parameter thereat.

The sensor assembly 100 further comprises a detection unit 109 mounted within the interior INT of the sensor assembly and configured to measure the displacement of the member 101 caused by the application of pressure to the contact surface 102 from the exterior of the sensor assembly.

The member 101 is held by a flexible membrane 110 so that a distal part 103 of the member 101 associated with the contact surface 102 is disposed at one side of the membrane 110 and a proximal part 105 of the member 101 associated with its proximal end 104 is disposed at the other, opposite side of the membrane 110. If the sensor assembly 101 is used in a disposition as shown in FIG. 1A, where its contact surface and the flexible membrane are oriented generally horizontally, the distal part 103 of the member 101 with the contact surface 102 itself is located below the membrane 110, and the proximal part 105 is located above the membrane 110. It is to be noted that the terms "below" and "above" are used for convenience purposes only and are not limiting in any way.

The flexible membrane 110 has a central area 121, at which the member 101 is held thereby, and a peripheral area 111 along which it is fixedly mounted to a static supporting structure 114 so as to allow the central area to flex along the central axis Z of the assembly, which in the present example constitutes an axis of symmetry of the member 101 and the flexible membrane 110. A plane X-Y defined by the membrane in its original state is perpendicular to the central axis Z. Any suitable fixation means can be used for the fixation of the circumferential periphery 111 of the flexible membrane 110 to the supporting structure 114 such as for example a glue, a plurality of fixation screws or bolts, or the like.

The member 101 can be in the form of a unitary body or it can be integrally assembled from a number of elements to function as a unitary body. Furthermore, the member 101 can be formed as an integral assembly with the flexible membrane 110. Alternatively, the membrane 110 can have an opening with a rim received within a corresponding groove of the contact surface holding member disposed between its distal and proximal parts (not seen). Member 101 can have a hollow structure and its internal space may be used to accommodate electric or optical components, or one or more biological sensors, e.g. a PPG and/or ECG sensor. In some embodiments, the biological sensor is a PPG sensor surrounded by an ECG electrode. The ECG electrode is typically made of stainless steel and can be coated with silver chloride or silver/silver chloride (Ag/AgCl) coating.

The proximal part 105 of the member 101 constitutes a base and its proximal end 104 constitutes a base surface, to which a part of the detection unit 109 is fixedly mounted so as to be moved together with the member 101 relative to another part of the detection unit 109 fixedly mounted to the supporting structure 114. In the present example the base surface 105 at least partially lies in a plane which is perpendicular to the central axis Z.

The detection unit 109 comprises a light source 106 and a detector 108 constituting a sensing unit 107 of the sensor assembly 100, and a light blocking member 112. The light source 106 and the detector 108 face each other along an optical axis O of the sensing unit 107, as can be best seen in FIG. 1B, such that light emitted from the light source 106, if not blocked, can be directly received by the detector 108. Namely, the light emitted from the light source 106 propagates freely, without any particular reflections, towards the detector 108.

In the present example, the sensing unit 107 constitutes the part of the detection unit 109 that is fixedly mounted to the base surface 104 of the contact surface holding member 101, and the light blocking member 112 constitutes the part of the detection unit 109 that is mounted to the supporting structure. The mutual disposition of the sensing unit 107 and the light blocking member 112 is such that the light source and the detector are located on two sides of the light blocking member 112 at least during blocking operation thereof. More particularly, the above mutual disposition is such that, when the sensing unit 107 moves together with the contact surface holding member 101 relative to the light blocking member 112 and the supporting structure 114, the position of the light blocking member 112 in the direction perpendicular to the optical axis O of the sensing unit 107 changes between a minimal blocking position, in which a minimum amount of light propagating from the light source 106 to the detector 108 reaches the detector, and a maximal blocking position, in which a maximal amount of light propagating from the light source 106 to the detector 108 is blocked. This results in the light received by the light detector to be indicative of the displacement of the contact surface 102.

The light source 106 can be of any type capable of continuous or pulsed emission of light, e.g. a LED or laser source, and the detector 108 can be of any type configured to detect at least a part of the light emitted by the specific light source. The light source 106 can be configured to emit light comprising any pre-determined wavelength band, e.g.

from the visible and non-visible parts of the spectrum, and the detector should be configured to detect light of such wavelength band. The detector thus can comprise at least one photodiode or phototransistor.

The sensing unit 107 can be configured so as to make sure that light reaching the detector 108 is only that coming directly from the light source 106. This can be achieved by at least one of the following:

providing the light source with a divergence angle reducing element configured to reduce a divergence angle of the light source in at least one plane comprising the optical axis O; or providing the detector with a field of view reducing element configured to reduce field of view of the detector in at least one plane comprising the optical axis O For example, the light source 106 can have an original diverging angle of 140 degrees in a first plane perpendicular to the central axis Z and a divergence angle of 140 degrees in a second plane perpendicular to the first plane, and it can be provided with the divergence reducing element to reduce at least one of these angles by 60 degrees In the present example, a divergence reducing element 122, having an open aperture 123, is used to reduce the divergence angle of the light source in the first plane while maintaining its original divergence angle in the second plane. In other words, in the present example, the horizontal divergence angle of the light source is reduced whilst its vertical divergence angle is maintained.

The detector 108 can have an original field of view of 160 degrees in the first plane perpendicular to the central axis Z and field of view of 160 degrees in the second plane perpendicular to the first plane, and it can be provided with a field of view reducing element to reduce at least one of these angles by 60 degrees In the present example, a field of view reducing element 120 having an open aperture 124 is used to reduce the field of view of the detector in the first plane while maintaining its original field of view in the second plane. In other words, in the present example, the horizontal divergence angle of the light source is reduced by the element 120 while its original vertical divergence angle is maintained, and the horizontal field of view of the detector is reduced by the element 122 while maintaining its original vertical field of view.

The divergence reducing element 122 is disposed adjacent the light source's transmitting region and it prevents light emitted from the light source 106 from reaching any elements of the assembly that can be disposed to the right or to the left from the optical axis O as seen from the direction of the light source. The field of view reducing element 120 is disposed adjacent the detector's detecting region and it prevents light other than that received directly from the light source from reaching the detector 108.

The light blocking member 112 has such dimensions in a plane perpendicular to the optical axis as to enable it to block to a desired maximal extent either the aperture 123 of the divergence reducing element 122 or the aperture 124 of the field of view reducing element 124 or both. In the present example, the blocking member 112 is disposed adjacent the light detector 108 and it is configured to block entrance of light into the detector to an extent depending on the position of the contact surface holding member 101 with the sensing unit 107 along the axis Z during operation of the sensor assembly.

More particularly, the light blocking member 112 has a blocking member edge 113, which is configured to be disposed at a maximal distance from the contact surface 102, when no pressure is applied to the contact surface 102 and the flexible membrane 110 is in its normal, non-flexed position. In this position, the light blocking member 112 is configured not to block or to only minimally block the light from the light source incident on the detector 108 and the amount light detected by the detector 108 is thus maximal. This position of the light blocking member will further be referred to as its 'minimally blocking state'.

When in operation pressure is applied on the contact surface 102 from the EXT in the direction Z, the central area 121 of the flexible membrane 110 flexes in the same direction, thus moving the contact surface holding member 101 in this direction, thereby gradually reducing the distance between the contact surface 102 and the light blocking member edge 113. This results in the light blocking member 112 gradually blocking more and more light from entering the detector 108 as the pressure on the contact surface 102 increases. The light blocking member 112 is thus configured to reach its 'maximally blocking state', in which a minimal amount of light reaches the detector 108, if at all, when the pressure on the contact surface 102 reaches a predetermined maximal level. In this state, the edge 113 of the blocking member 113 is brought to a minimal distance from the contact surface 102 of the contact surface holding member 101.

In order to increase the range of possible movement of the sensing unit 107 relative to the light blocking member 112 and thus allow reaching the maximal or full blockage of light received by the detector 108, without increasing corresponding dimensions of the sensor assembly 100 along the axis Z, the contact surface holding member 101 can be configured to allow a portion of the light blocking member 112 with its edge 113 to be received in a corresponding groove, slit or any other receiving space extending within the contact surface holding member 101. FIGS. 2A to 3B schematically illustrate two examples of such design of the contact surface holding member. In the figures throughout the application, like elements of different figures were given similar reference numerals shifted by the number of hundreds corresponding to the number of the figures. For example, element 204 in FIGS. 2A and 2B serves the same function as element 104 in FIGS. 1A-1D.

Figure 2A:
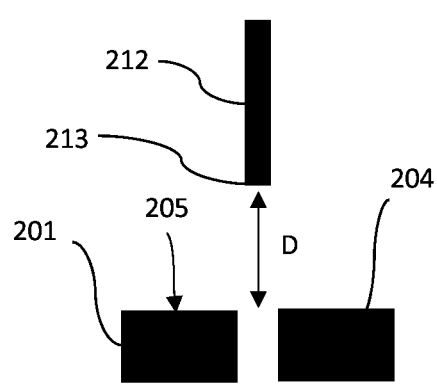
FIGS. 2A and 2B are schematic illustrations of the relative movement of a blocking member with respect to a contact surface holding member of a sensor assembly according to another example of the present disclosure.
Figure 3A:
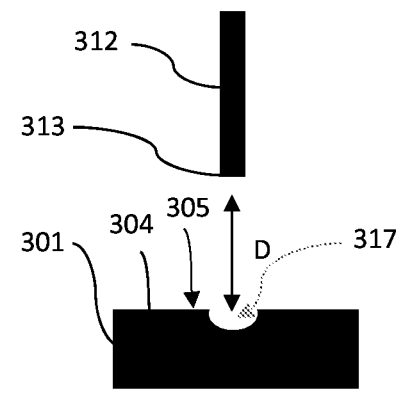
FIGS. 3A and 3B are schematic illustrations the relative movement of a blocking member with respect to a substrate of a sensor assembly according to a still further example of the present disclosure.
Figure 2B:
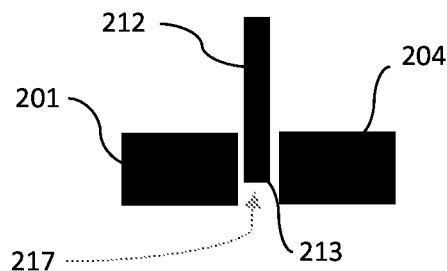
Figure 3B:
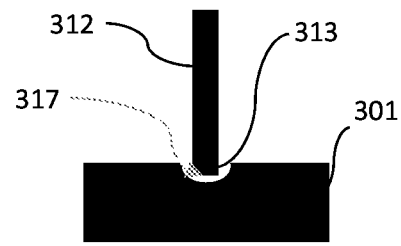

Thus, in FIGS. 2A-2B and 3A-3B, the proximal parts 205 and 305 of the contact surface holding members 201 and 301 with their proximal ends 205 and 305 are shown as having a receiving space, which is in the form of a slit 217 and a depression 317 extending from the proximal end 204, 304 of the contact surface holding member 201, 301 into its interior and configured to receive therein the light blocking member 212 and 312 with its edge 213, and the light blocking member 312 with its edge 313, respectively. FIGS. 2A and 3A illustrate a minimal blocking state of the blocking members 212 and 312, in which a distance D between the blocking member edge 213, 313 and the contact surface 202, 302 is maximal, and FIGS. 2B and 3B illustrate a maximal blocking state of the blocking members 212 and 312, in which the distance D between the blocking member edge 213 and the contact surface 202, 203 is minimal.

The sensor assembly described above, as well as any other sensor assembly according to the presently disclosed subject matter, can be used in a measuring device configured for measuring at least one biological parameter of a patient by contacting the patient's skin surface. The measuring device can thus comprise a biological parameter measuring sensor, such as e.g. photoplethysmograph (PPG) sensor, configured to be brought into contact with the patient's skin surface for measuring the biological parameter thereat. Such biological parameter can be, for example, a heart rate and/or heart rate variability. Since measurements performed by a biological parameter measuring sensor can be affected by the pressure occasionally applied to the measurement device by the skin surface, a sensor assembly according to the presently disclosed subject matter can be used to continuously measure and monitor displacements of the biological parameter measuring sensor, thereby allowing artifacts identified thereby to be taken into consideration in the analysis of the measured biological parameter/s, due to which accuracy of the measurements of the biological parameter/s can be essentially increased.

Thus, in accordance with the presently disclosed subject matter there is provided a measuring device of the above kind, comprising a biological parameter measuring sensor and a displacement sensor assembly of the kind described above with reference to FIGS. 1A to 3B, with a difference being in that, the contact surface of the displacement sensor assembly of the measuring device is configured to incorporate the biological parameter measuring sensor. The latter sensor can be a PPG sensor of the kind described in US 2017/0020399, whose description is incorporated herein by reference.

Figure 4:
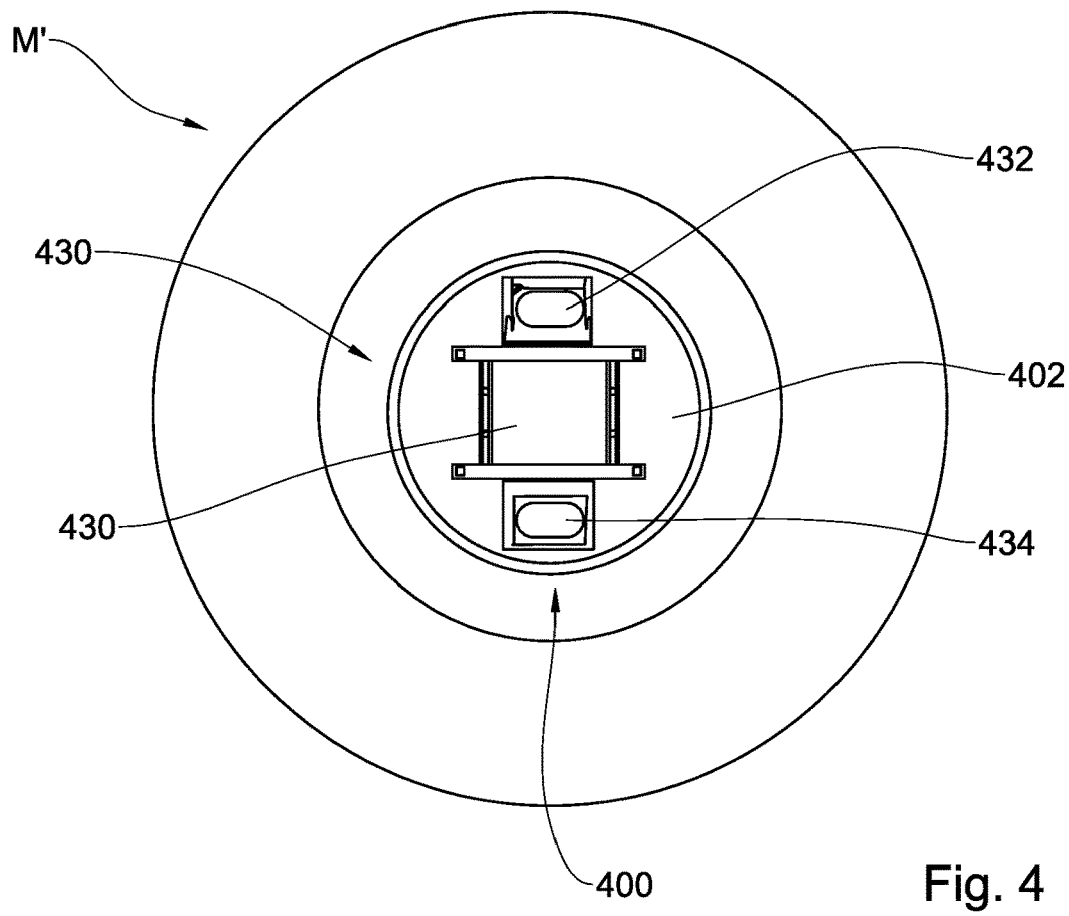
FIG. 4 is a schematic bottom view of a measuring device, according to a further example of the present disclosure.
Figure 5:
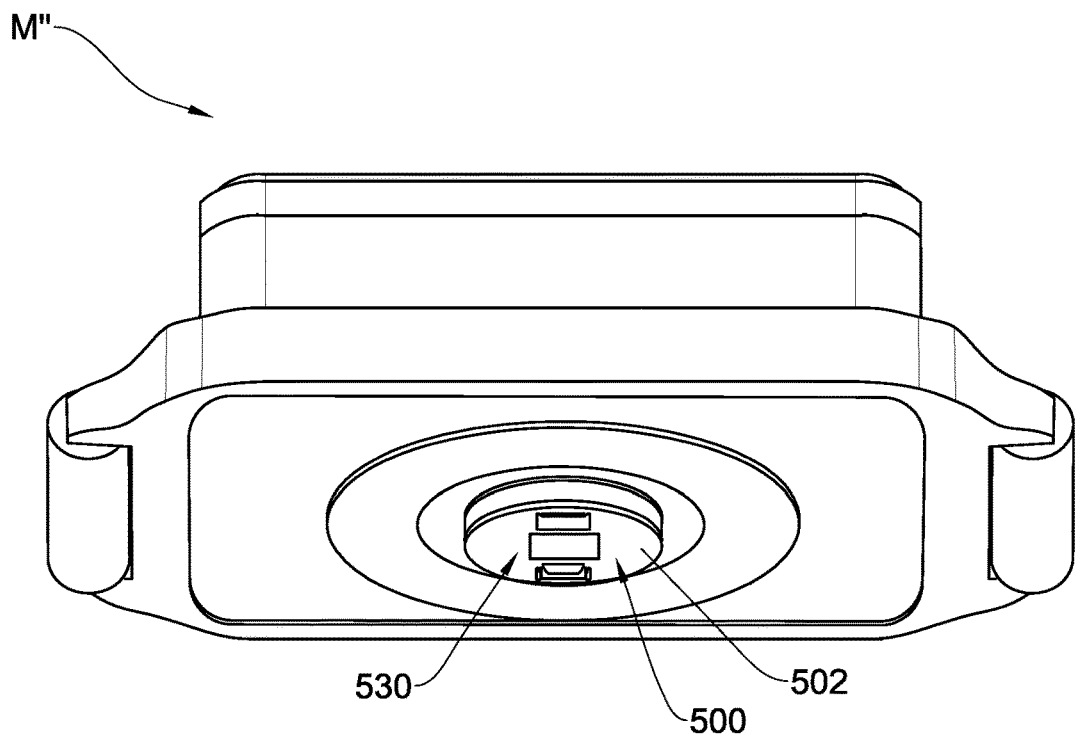
FIG. 5 is perspective bottom view of a measuring device according to a still further example of the present disclosure.

FIGS. 4 and 5 illustrate examples of such measuring devices M' and M" each comprising a PPG sensor 430, 530 and a displacement sensor assembly 400, 500 having a contact surface 402, 502, respectively, which incorporates the PPG sensor. As best seen in FIG. 4, the PPG sensor in this example comprises two LED light sources 432 and 434 and a photodiode detector 436 therebetween, all mounted to the contact surface 402 and constituting an integral part thereof for the purpose of its functioning as a part of the displacement sensor assembly of the measuring device M'. In FIG. 5 the measuring device M" is in the form of a wrist watch, in which the biological sensor 530 is mounted to and constitutes a part of the contact surface 502.

Figure 6:
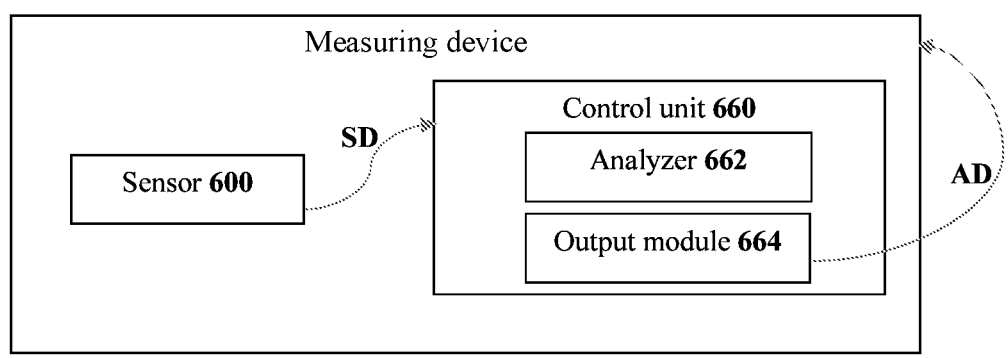
FIG. 6 is a block diagram illustrating operational components of a measuring device of the kind shown in FIGS. 4 and 5.

As schematically illustrated in FIG. 6, each of the above measuring devices M' and M" can comprises, in addition to the biological parameter measuring sensor and the displacement sensor assembly, a control unit 660 comprising an analyzer 662 that is configured to analyze data SD sensed by the biological parameter measuring sensor and by the sensor assembly to identify the artifacts therein and generate analyzed data AD indicative thereof. The measuring device illustrated in FIG. 6 further comprises an output module 664 configured to communicate the analyzed data AD to a data storage device or a processor for further processing thereof. When the measuring device is in the form of a wrist watch, the analyzed data AD can be communicated to the wrist watch and can undergo further processing. It is to be noted that the analyzed data AD can comprise compensation data for compensating the undesired sensed artifacts.

Figure 7A:
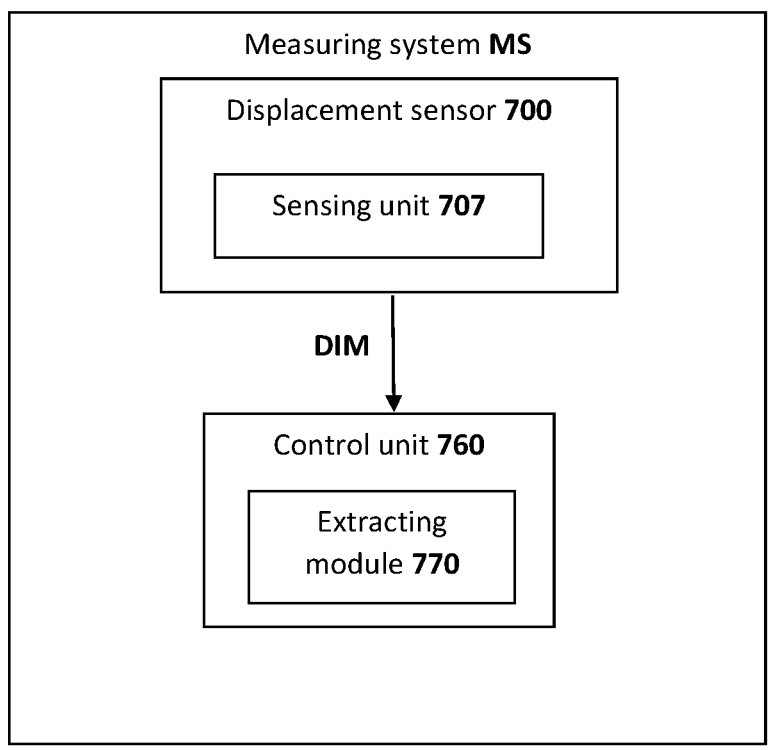
FIGS. 7A-7B are block diagrams illustrating operational components of a measuring system including displacement sensor according to the present disclosure.
Figure 7B:
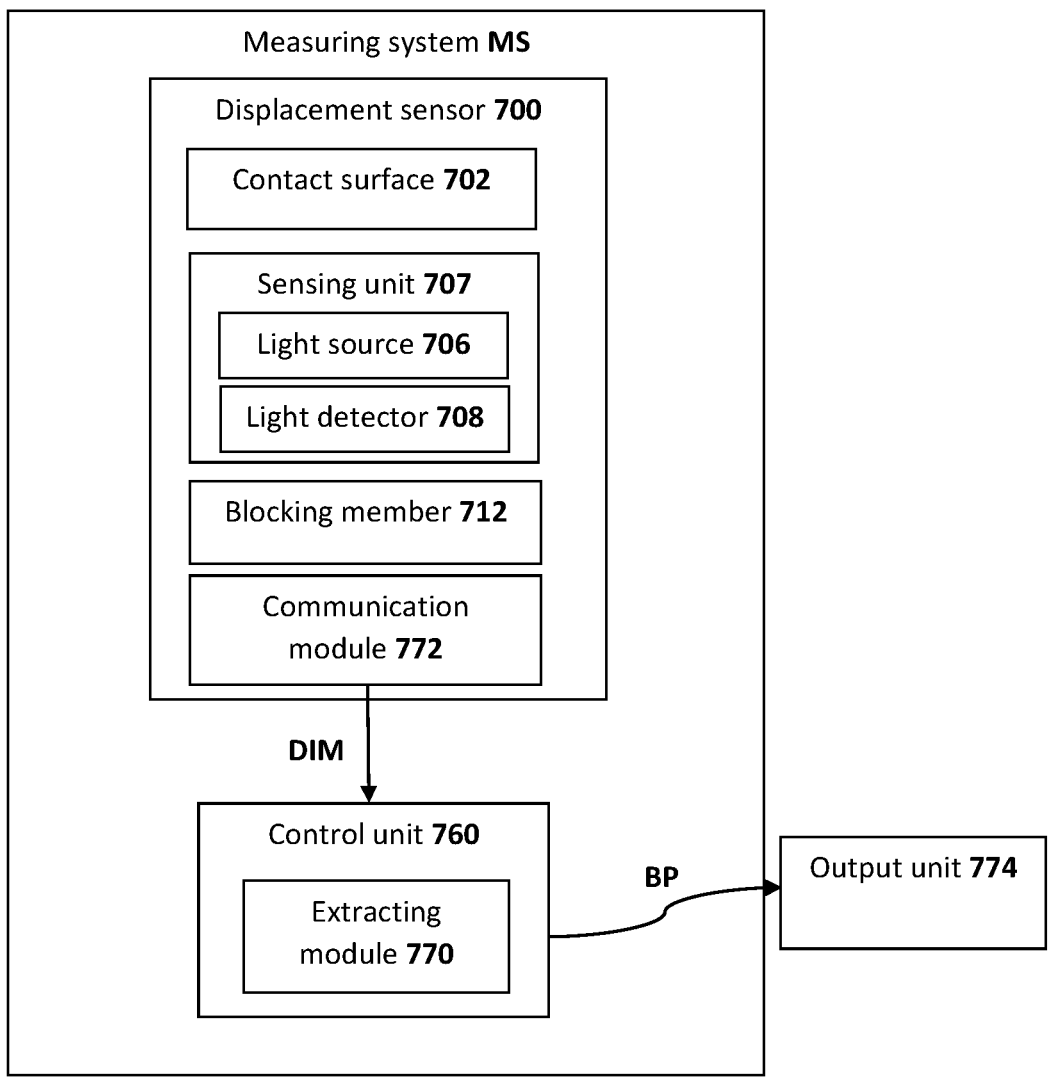

Reference is now made to FIGS. 7A-7B which provide a block diagram of a measuring system for measuring a biological parameter in accordance with embodiments of the present disclosure. The measuring system MS comprises a displacement sensor 700 that includes a sensing unit 707 and is configured to collect data indicative of movement (DIM) of the skin. DIM is communicated to a control unit 760 the comprises an extracting module to analyze and extract the biological parameter from the DIM. As shown in FIG. 7B, displacement sensor 700 configured to contact the skin surface of a subject through a contact surface 702 to obtain DIM of the skin of the subject. In accordance with this embodiment, the displacement sensor 700 comprises sensing unit 707 that includes a light source 706 and a light detector 708, the light source is configured to emit light directly towards the light detector 708.

Displacement sensor 700 also includes a blocking member 712 that is configured to block a portion of the light emitted from light source 706 towards light detector 708 according to movement of contact surface 702 or the pressure applied thereon. In that manner, light detected by light detector 708 is indicative of the displacement of contact surface 702 with respect to movement of the skin surface. Displacement sensor 700 collects DIM of the skin and a communication module 772 communicates the DIM to a control unit 760, either by wired or wireless connection. The control unit may be a part of wrist watch processing unit or a remote computing unit, e.g. a mobile phone or a cloud-based computing unit.

Control unit 760 comprises an extracting module 770 configured to analyze the DIM and extract one or more biological parameters BP therefrom.

The BP may be communicated to an output unit 774 that outputs the biological parameter, e.g. visually on a monitor, vocally through speakers and/or as a print out.

Figure 12:
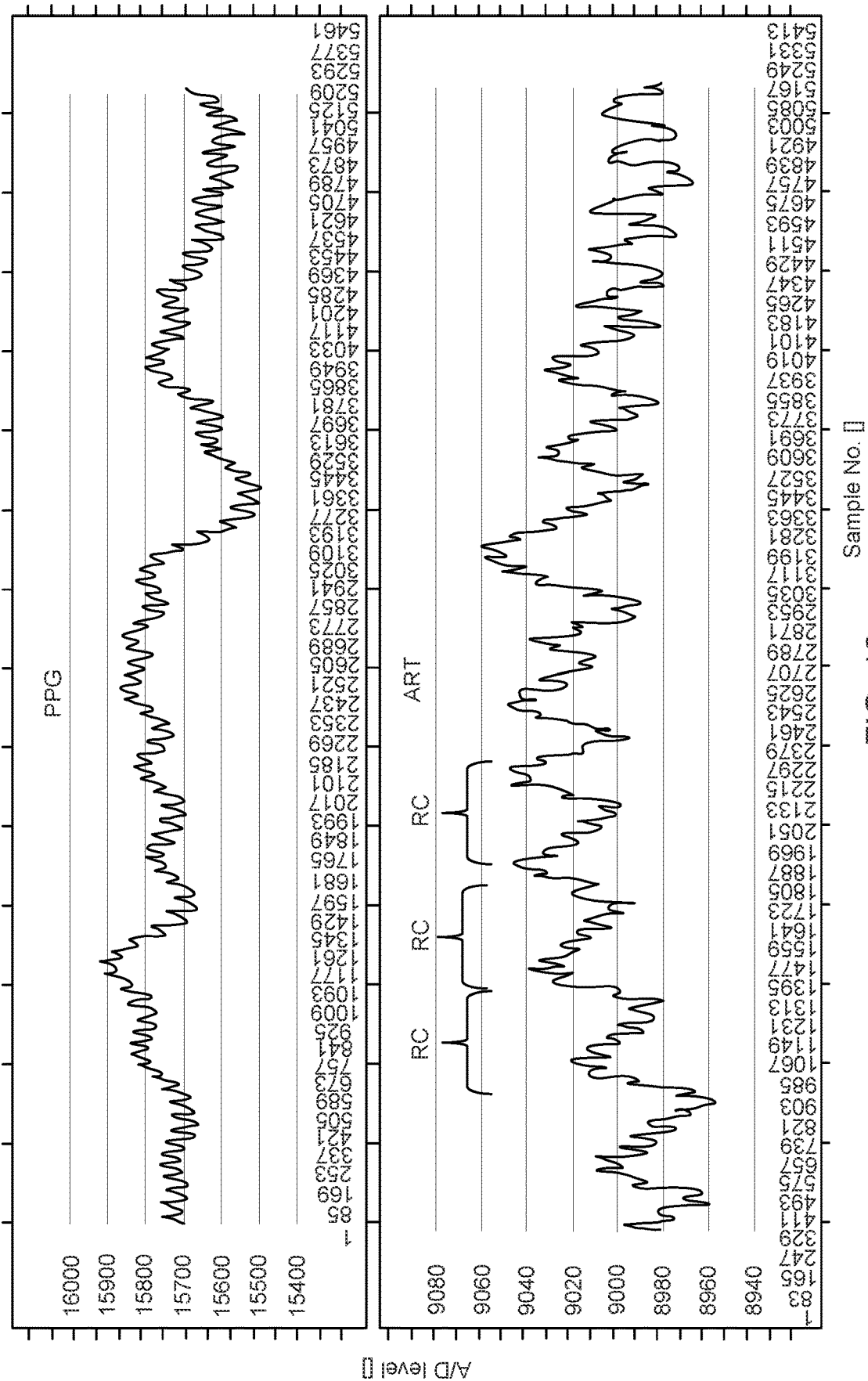
FIG. 12 is an example of comparative results of signals obtained from the skin of a subject between a PPG sensor and the displacement sensor of the present disclosure.

As an illustration for the use of a displacement sensor of a kind disclosed herein, FIG. 12 provides a signal comparison received by a PPG sensor (the upper signal) and the displacement sensor (the lower signal) of measurement taken from the radial artery. Based on this data, respiration cycles RC are extracted by analyzing the DC signal or extracting the AC signal by a predetermined signal filter similarly, other biological parameters can be extracted such as heart rate and/or blood pressure.

Figure 13A:
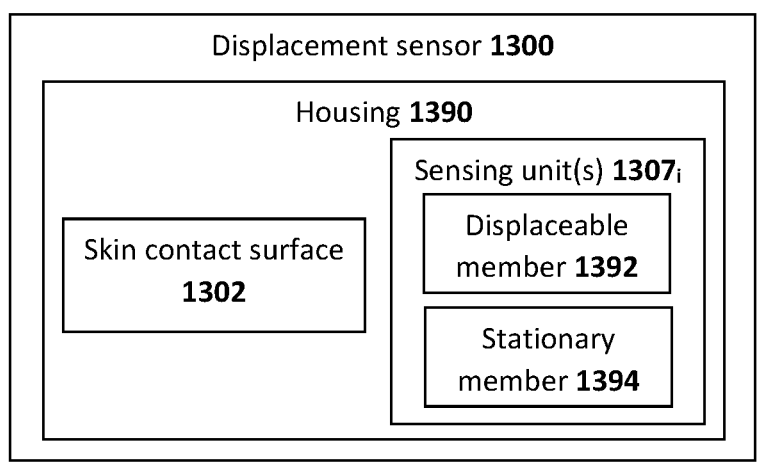
FIGS. 13A-13B are block diagrams of non-limiting example of embodiments of a displacement sensor and measuring device according to the present disclosure.
Figure 13B:
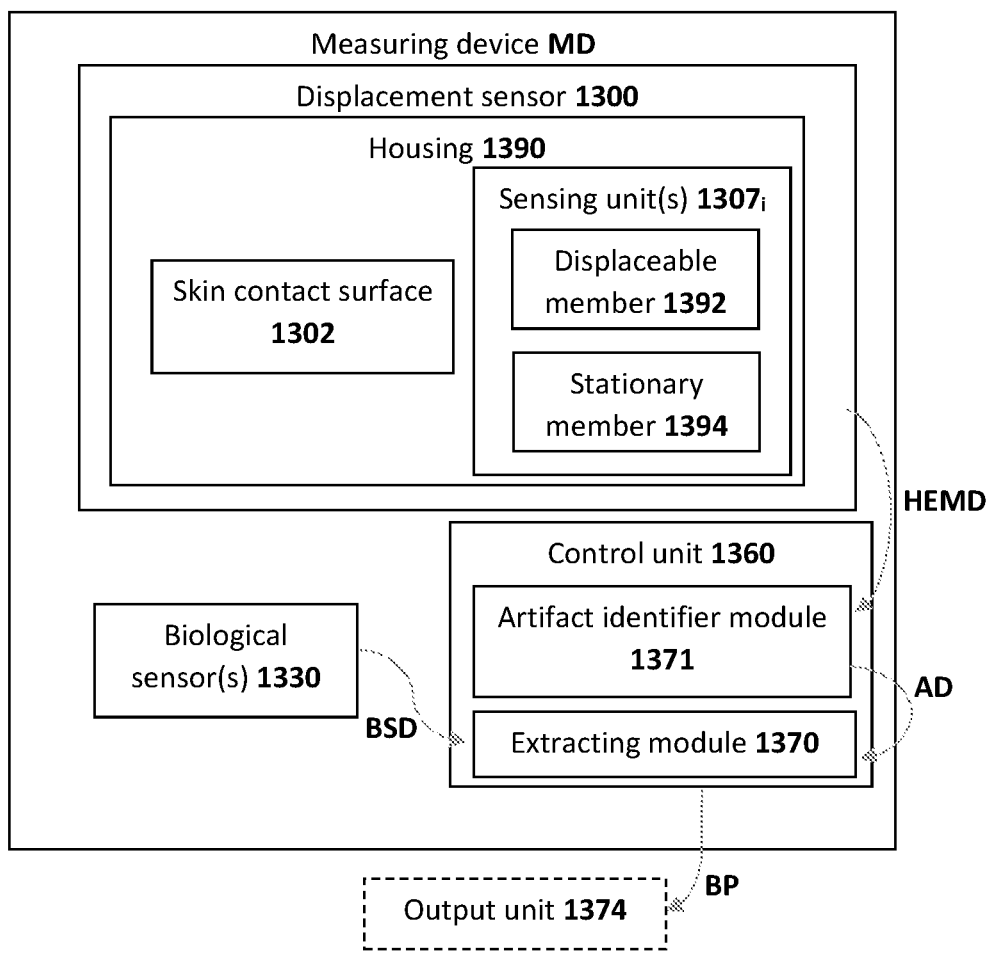

Reference is now made to FIGS. 13A-13B which are block diagrams of non-limiting examples of embodiments of a displacement sensor and measuring device according to the present disclosure. FIG. 13A shows a displacement sensor 1300 that is based on measurement of a Hall-effect sensor. The displacement sensor 1300 includes a housing 1390 that defines a volume that comprises the elements of the displaceable sensor 1300. A skin contact surface 1302 is configured to be brought into contact with the skin of a subject and is displaceable with respect to the housing 1390 along at least one axis. Typically, the displacement of the contact surface 1302 is along a vertical axis that is perpendicular to a plane spanned by the contact surface 1302. In some embodiments, the contact surface 1302 has more degrees of freedom with respect to the plane to thereby allow tilt and roll with respect to the plane. The contact surface 1302 is responsive to application of force profile thereon, e.g. by pressure applied by expansion and contraction of blood vessels at the vicinity of the skin surface, to perform displacement that is proportional to the amount of applied force. One or more sensing units $1307_i$ (where 'i'=the number of sensing units) are configured to sense the displacement of the contact surface and provide data thereof. Each of the sensing units $1307_i$ includes a Hall-effect sensing pair, wherein one is a constant magnet and the other is a Hall-effect sensor. The sensing pair provides a Hall-effect measurement data that is corresponding to the gap between members of the sensing pair. The Hall-effect measurement data typically comprises voltage data that is indicative of a gap/distance between the members of the sensing pair. One of the members is a displaceable member 1392 that is displaceable together with the skin contact surface 1302 and the other is a stationary member 1394 that is stationary with respect to the housing 1390 and does not move when pressure applied on the contact surface 1302. The two members define a non-biased gap therebetween which is the gap when no pressure is applied on the contact surface 1302, namely a reference, steady state of the displacement sensor 1300. When pressure is applied on the contact surface 1302, the contact surface and the displaceable member are displaced together, and the gap between the sensing pair varies, e.g. decreases. The Hall-effect measurement data that is then provided by the sensing unit 1307$_i$ is indicative of the displacement of the contact surface 1302.

FIG. 13B shows an embodiment of a measuring device MD that includes a displacement sensor 1300. The measuring device MD further includes a biological sensor(s) 1330 and a control unit 1360 that is in data communication with the sensing unit(s) 1307$_i$ and configured to receive a Hall-effect measurement data HEMD therefrom. The biological sensor(s) 1330 may include an optical sensor, e.g. PPG, or an electrical sensor, e.g. ECG. The biological sensor(s) 1330 is configured to sense parameters that are indicative of biological parameters of the subject and generate biological sensing data BSD based thereon. The biological sensor(s) transmits the biological sensing data BSD to the control unit 1360 for processing and extracting a biological parameter BP of the subject. An artifact identifier module 1371 of the control unit 1360 receives the Hall-effect measurement data HEMD and generates artifact data AD based thereon that is indicative of artifact movements of the skin surface that are sensed by the displacement sensor 1300. The artifact identifier module 1371 transmits the artifact data AD to an extracting module 1370 that is configured to extract biological parameter BP based on the artifact data AD and the biological sensing data BSD. Optionally, the biological parameter is communicated to an output unit 1374.

It should be noted that system elements from FIGS. 13A-13B may be combined between them to provide the displacement sensor or the measuring device of the present invention.

Figure 14:
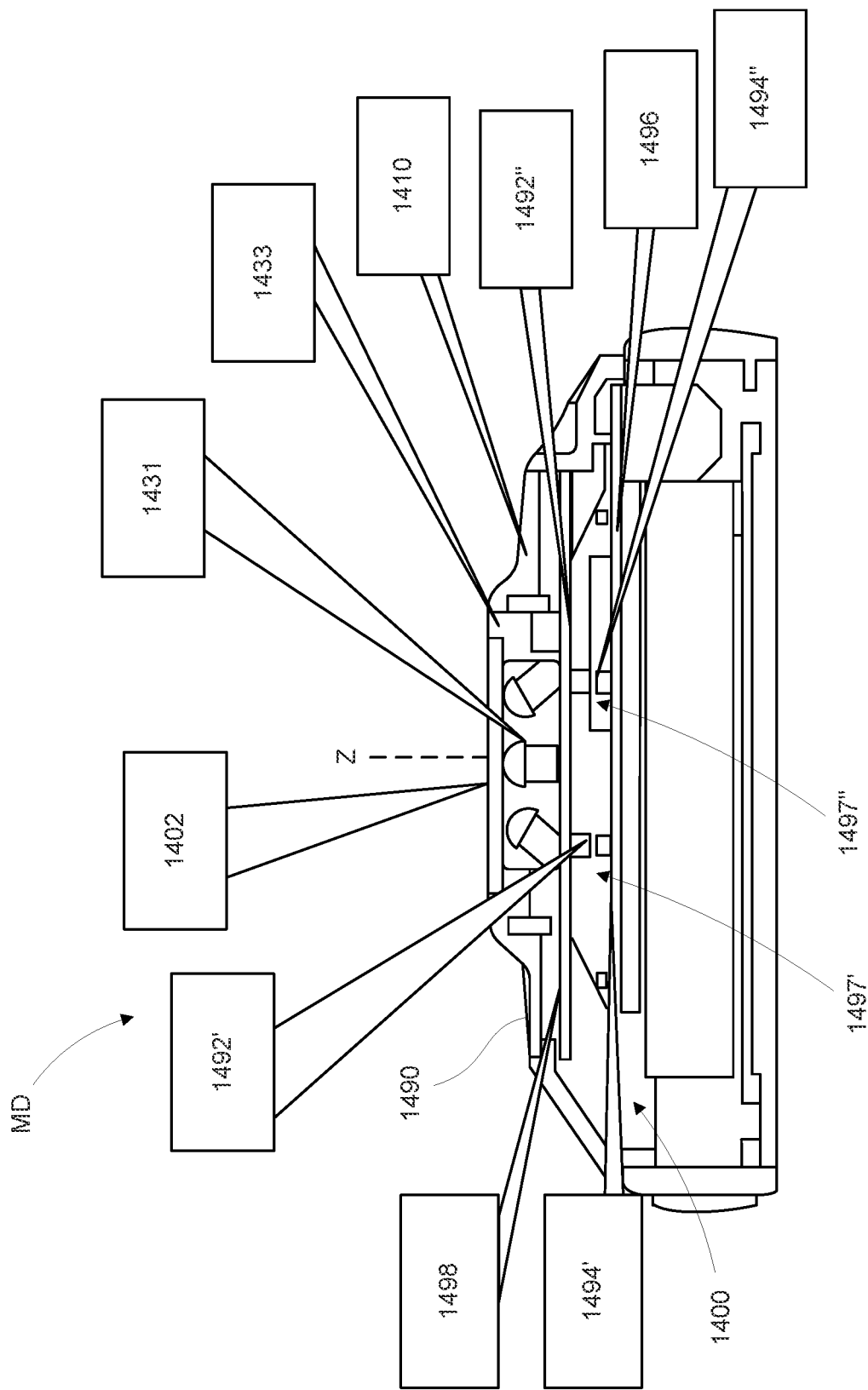
FIG. 14 is a schematic cross-sectional view of a non-limiting example of an embodiment of the Hall-effect based displacement sensor according to the present disclosure.

FIG. 14 is a schematic cross-sectional view of a non-limiting example of an embodiment of the Hall-effect based displacement sensor that is integrated into a measuring device for measuring biological parameters. Measuring device MD comprises displacement sensor 1400 that includes a housing 1490 that is integrated with a skin contact surface 1402. The contact surface 1402 is displaceable together with a displaceable plate 1498, which displaceable members 1492' and 1492" of Hall-effect sensing pairs are formed thereon. Stationary members 1494' and 1494" are formed on a stationary plate 1496, e.g. a PCB of the motherboard of the measuring device MD. Each displaceable member 1492', 1492" and their respective Stationary members 1494', 1494" constitute a Hall-effect sensing pair. Gaps 1497' and 1497" that are spanned between displaceable members 1492', 1492" and stationary members 1494', 1494" of each Hall-effect sensing pair are varied with the displacement of the contact surface 1402 and the displaceable plate 1498. Hall-effect measurement data that is generated by each sensing pair is indicative of the displacement of the contact surface 1402 that is resulted from skin movement of the subject. In an exemplary embodiment, the displaceable members 1492' and 1492" may be configured as constant magnets and stationary members 1494' and 1494" may be configured as Hall-effect sensors.

The contact surface 1402 is attached to the housing 1490 by a flexible member 1410 that allows the movement of the contact surface 1402 at least along axis Z that is generally perpendicular to a plane spanned by the contact surface 1402. In some embodiments, the flexible member 1410 is configured to allow the contact surface to tilt or roll with respect to a plane spanned by the contact surface 1410 in a steady state. Namely, in the instance that uneven pressure is applied on the contact surface 1410, some portions thereof are biased to one side of the plane and other portions are biased to the other side of the plane.

An optical sensor 1410, e.g. a PPG sensor, is attached to the displaceable plate 1498 and displaceable therewith. The optical sensor 1410 is configured to obtain optical measurements through the contact surface 1402 that are indicative of physiological parameters of the subject, e.g. heart rate, blood pressure or respiration rate. An electrical sensor 1433, e.g. an ECG sensor, is formed on the housing 1490 and is configured to provide electrical-based measurements indicative of physiological parameters of the subject.

Figure 8A:
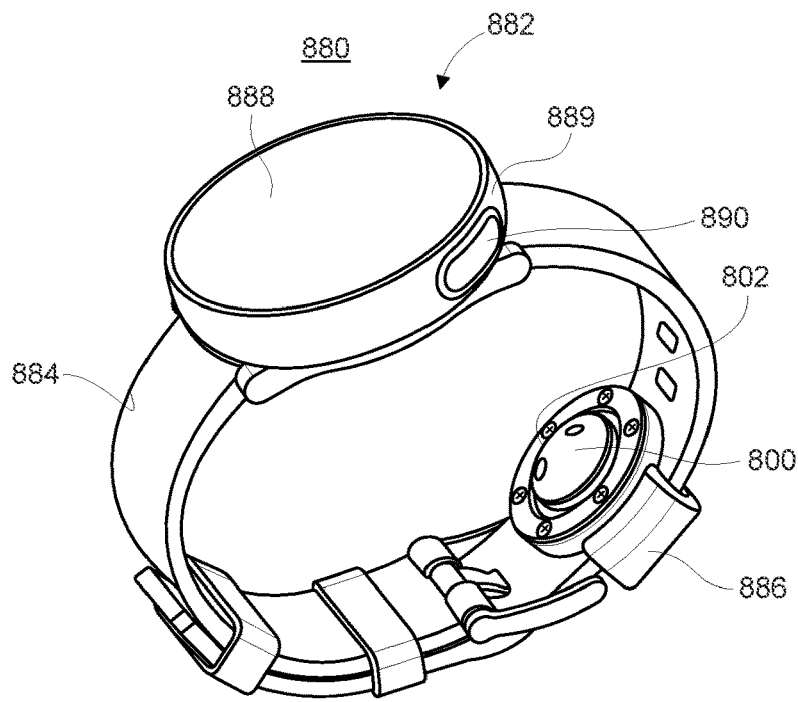
FIGS. 8A-8B are schematic perspective views of examples of the system of the present disclosure integrated into a wrist watch.
Figure 8B:
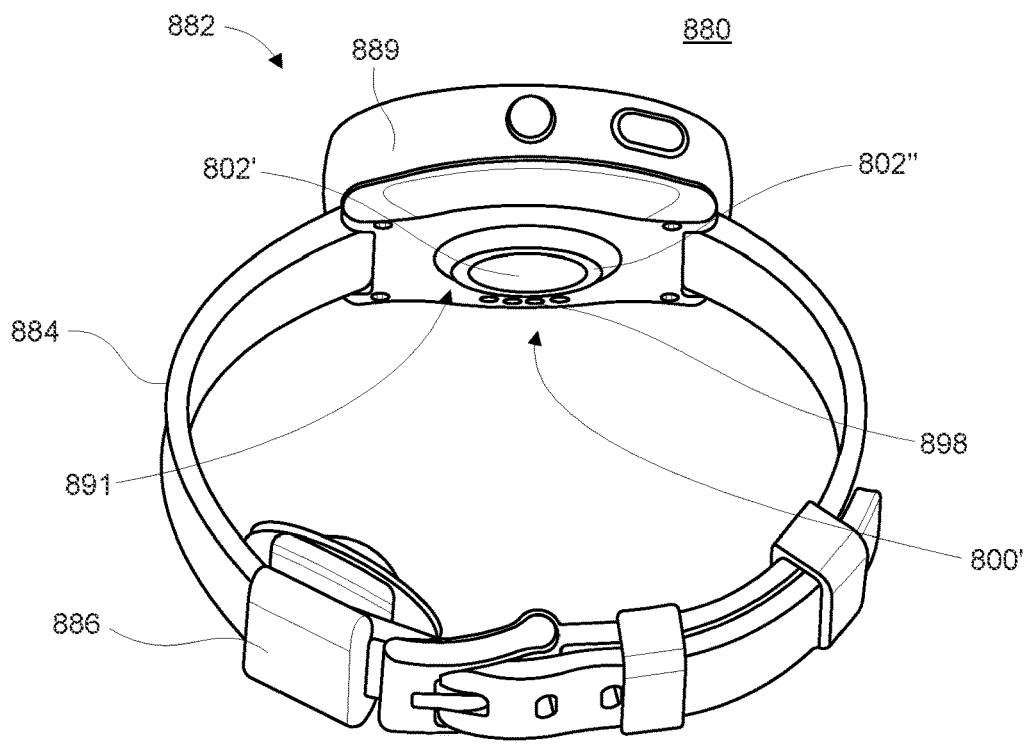

Reference is now made to FIGS. 8A-8B that provide a schematic perspective view of a measuring system 880 of any of its embodiments as disclosed herein, integrated into a wrist watch 882. According to this embodiment, displacement sensor 800 is clipped onto a wristband 884 by a fixation element 886 illustrated in this exemplary embodiment as a clip, best shown as element 986 in FIGS. 9A-9B.

Sensor assembly 800 comprises contact surface 802 placed along wristband 884 so as to be fixed in proximity, or precisely over the radial artery, when worn on the wrist of the subject.

The displacement sensor 800 has in this embodiment a curved contact surface 802 with a generally hemispheric shape. Without being bound by theory, it is considered that this curved contour may allow the contact surface 802 to fit into a body depression proximal to the radial artery of the subject thereby increasing the sensitivity and thus accuracy of the sensor.

The extracted biological parameter may then be presented on a display unit 888. In some embodiments, display unit 888 is integral into a watch.

Wrist watch 882 may comprise an additional displacement sensor illustrated in FIG. 8B as element 800', placed at the bottom side, opposite to the display unit 888 of the main body of the watch 889 having its contact surface facing the wrist of the subject when worn thereon. Contact surface 802' is a joint surface of displacement sensor 800' and an optical biological sensor, e.g. a PPG sensor embedded within the wrist watch 882. In this exemplary embodiment, contact surface 802' would then be formed of transparent or translucent materials so as to permit the transmission of light illuminated from and received by the optical biological sensor.

In some embodiments, the additional displacement sensor 800' may be included in a sensor set 891, some may have a shared sensing surface and some may have a functionally independent sensing surface. As illustrated in FIG. 8B, the sensor set 891 includes two circular contact surfaces 802' and 802", one having a shape of a circular disc, with a diameter smaller than that of the other contact surface 802", the latter having a shape of a ring continuously surrounding and confining the disc-shape surface, the two shapes are co-centric. The sensors set 891 may include an optical biological sensor, e.g. a PPG sensor, a displacement sensor, the optical sensor and the displacement sensor having a shared sensing surface, and an electric based biological sensor, e.g. an ECG sensor, having its independent sensing surface surrounding the shared sensing surface.

A second ECG electrode is formed at the periphery of main body 889, as seen best in FIG. 8A, so as to permit, together with a first ECG sensor 802" that is disposed at the bottom of main body 889 an ECG measurement. First electrode 802" is configured to be in contact with a wrist of a first hand of a subject and the second electrode 890 is configured to brought into contact with a finger of a second hand of the subject to obtain the ECG measurement.

Further illustrated in FIG. 8B are electrical connectors 898 in this illustration, in a form of pogo pins for enabling updates of the software application of the control unit of the display unit 888 or for charging the same.

Figure 9A:
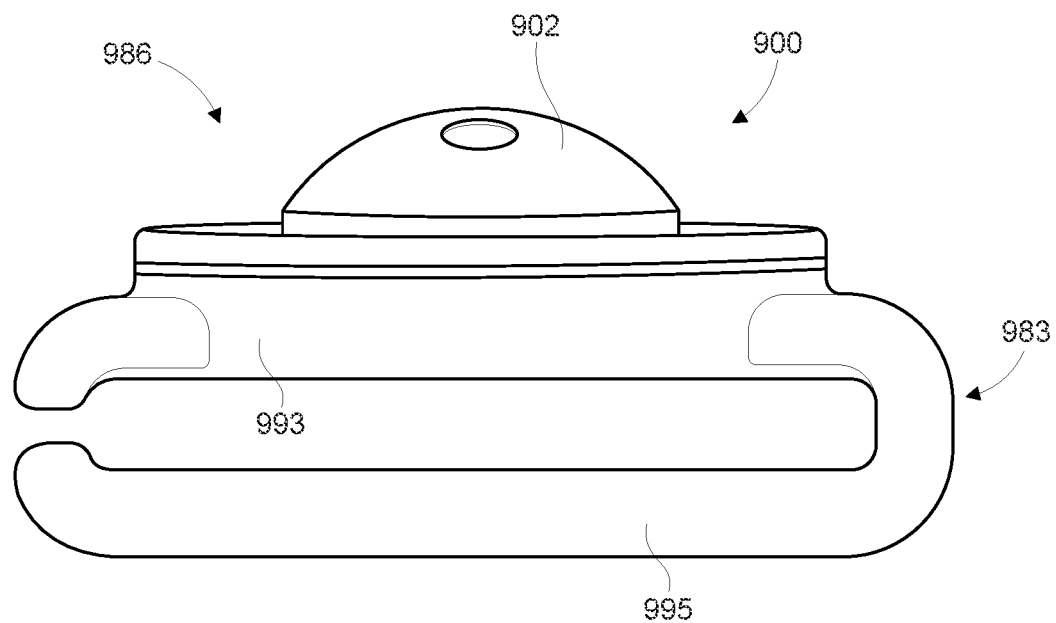
FIGS. 9A-9B are schematic side views of examples of a fixation element in a form of a clip comprising the displacement sensor of the present disclosure.
Figure 9B:
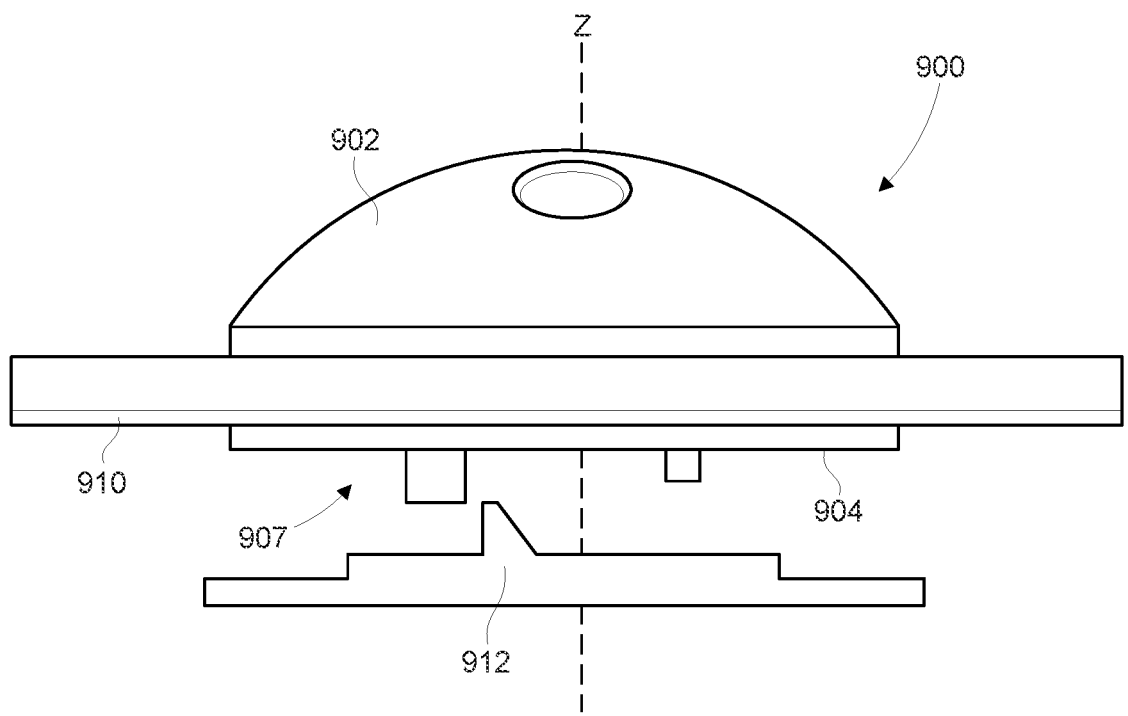

Reference is now made to FIGS. 9A-9B providing a schematic illustration of side views of a clip 986 for attaching displacement sensors, such as those illustrated in FIGS. 8A-8B to a band.

FIG. 9A differs from FIG. 9B in that the latter is showing the interior elements of the clip. In this non-limiting example, the displacement sensor integrated into the clip is the light-based embodiment, however the Hall-effect based displacement sensor can be integrated into such clip as well.

A flexible membrane 910 is fixedly attached to contact surface 902 in its one side and to a base surface 904 in the other, on which the sensing unit 907 is mounted. The flexible membrane allows contact surface 902 and sensing unit 907 to move at least along the axis Z therewith, and the blocking member 912 remains stationary. The displacement sensor 900 is comprised within the clip 986 and the clipping arrangement 983 is configured to fix the displacement sensor 900 on a desired position along a wristband of a wrist watch. The clipping arrangement 983 has a first and a second clipping members 993 and 995 respectively. The first clipping member 993 comprises the displacement sensor 900, part of it is housed within the interior of the member 993, the sensing unit 907 and the blocking member 912, and the contact surface 902 protrudes therefrom.

Figure 10:
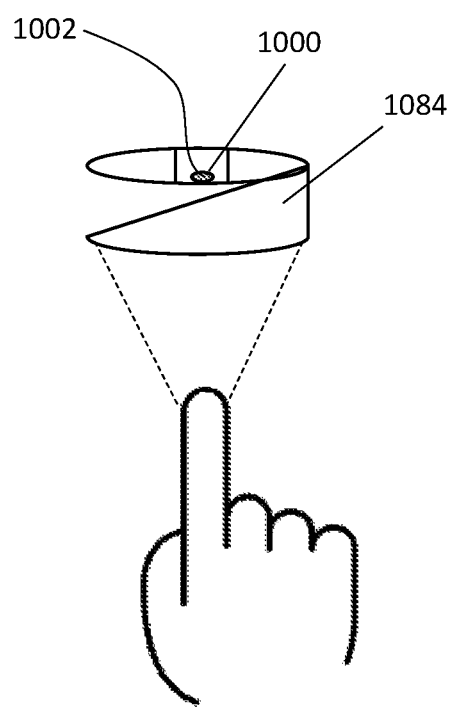
FIG. 10 is a schematic illustration of an example of fixation of the displacement sensor of the present disclosure onto a ring-shaped element.

Another example for fixing a displacement sensor of a kind disclosed herein, over an artery is shown in FIG. 10. Displacement sensor 1000 is fixed on the interior side of a ring shaped element 1084 that is configured to be worn on a finger of the subject and allow contact between contact surface 1002 and the subject's skin surface The ring-shaped element 1084 can be have constant dimensions or it can be adjustable to fit over various finger sizes. As finger arteries are located on the side thereof, preferably that the contact surface 1002 of the displacement sensor 1000 is placed on the side of the finger. The ring-shaped element 1084 may comprise a sensor set 1091 including a PPG and ECG sensor as described with respect to FIGS. 8A-8B. The external side of the ring-shaped element 1084 may comprise a second ECG electrode configured to be brought into contact with a finger of a second hand on which the ring in not worn. This may allow to support measurement of blood pressure and other parameters such as Pulse Transit Time.

Figure 11:
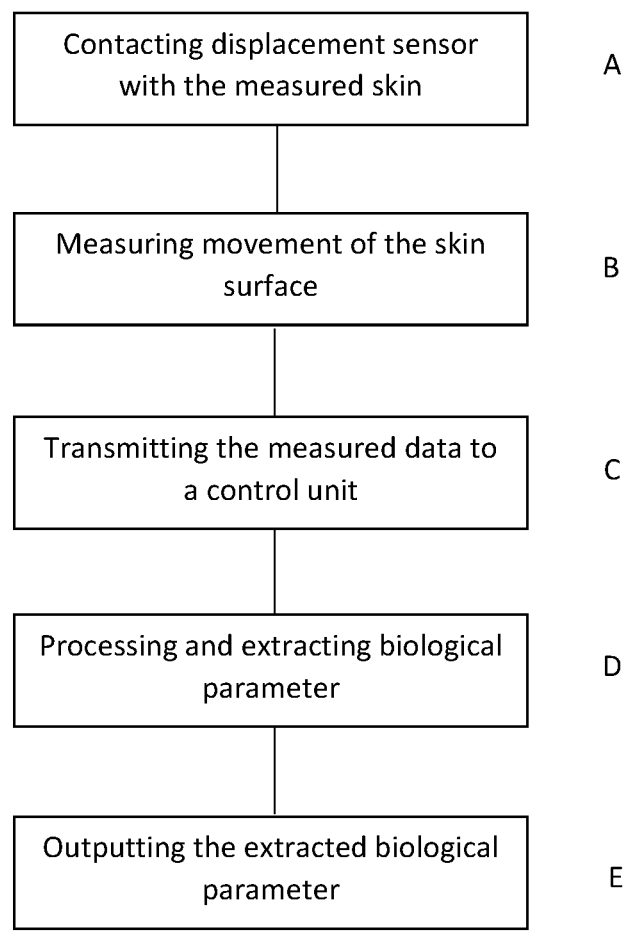
FIG. 11 is a block diagram exemplifying the flow of the method for measuring a biological parameter of a subject according to an embodiment of the present disclosure.

Turning now to FIG. 11, there is provided a block diagram illustrating a method of determining one or more biological parameters making use of a displacement sensor and/or a system in any one of their embodiments as disclosed herein.

Specifically, at first, a displacement sensor is brought into contact with a subject's skin A at a location proximal or over the artery. Once in place, in B, movement of the skin surface is detected. The measured data is transmitted in C to a control unit for further extracting therefrom, as indicated in D, one or more biological parameters. The extracted biological parameter may be outputted as a final E, e.g. on a display unit, by vocal means or as a print out.

The invention claimed is:

1. A system for determining a biological parameter of a subject, the system comprising:
(i) a displacement sensor comprising:
  a contact surface configured to contact skin surface of the subject;
  a sensing unit having at least one light detector and at least one light source with an optical axis defined between them, the light source being configured to emit light directly toward the sensor which is configured to detect the light; and
  a light blocking member associated with the sensing unit, such that displacement of the contact surface induces the blocking member to block light propagating along said axis in a manner proportional to the displacement of the contact surface, in response to pressure change of the skin on the contact surface, to obtain data indicative of displacement of the contact surface;
(ii) a control unit in data communication with the displacement sensor for receiving data indicative of said movement of the contact surface; said control unit comprises extractor module for extracting the biological parameter from the data indicative of movement of a skin surface; and
(iii) an optical biological sensor having a common contact surface with the displacement sensor.

2. The system of claim 1, wherein the biological parameter comprises blood pressure, heart rate, oxygen saturation or respiration rate; and wherein the extractor configured and operable for at least one of (i) applying at least one of pulse pressure wave analysis models, (ii) identifying the DC component of the data; or (iii) applying a signal filter.

3. The system of claim 1, further comprising an electric-based biological sensor that comprises a sensing surface continuously surrounding the contact surface of the displacement sensor.

4. The system of claim 1, further comprising a first displacement sensor and a second displacement sensor, at least one of the first and second displacement sensors is in data communication with an optical biological sensor and having a common contact surface therewith, and being configured for providing said optical biological sensor data indicative of the movement of the common sensing surface.

5. A measuring device comprising the system of claim 1.

6. The measuring device of claim 5, wherein the measuring device is configured as a wristwatch or in the form of a ring-shaped element configured to be worn on a finger of a subject.

7. A measuring device, comprising:
at least one biological sensor; and
a displacement sensor assembly, configured to increase accuracy of operation of the at least one biological sensor, the at least one biological sensor being configured for optically measuring at least one biological parameter of a user
wherein the displacement sensor assembly is configured for use in measuring a biological parameter at the skin of a user, the displacement sensor assembly comprising:
a skin contact surface facing towards an exterior of the assembly and configured for contacting the skin of a user, and movable along a central axis of the assembly in response to pressure change at the skin;
a sensing unit disposed within an interior of the assembly and having an optical axis lying in a plane perpendicular to the central axis of the assembly; the sensing unit comprises a light source configured to emit light along the optical axis and a light detector facing towards the light source and configured to detect light emitted by the light source directly towards the detector; and
a light blocking member operative to change the amount of light reaching the detector directly from the light source in consequence with displacement of the contact surface, whereby the light received by the light detector being indicative of the displacement of the contact surface.

8. The measuring device of claim 7, wherein the displacement sensor assembly further comprising a contact surface holding member having a central axis perpendicular to the contact surface, the contact surface holding member being movable along said central axis when pressure is applied to the contact surface from the exterior of the assembly.

9. The measuring device of claim 8, wherein the contact surface holding member has the contact surface at its distal end and a base surface at its proximal end spaced from the distal end along the central axis, and the assembly further comprises a static supporting structure, and wherein one of the sensing unit and the light blocking member is fixedly mounted to the base surface and is thus movable together with the contact surface holding member, and the other of these members is fixedly mounted to the static supporting structure; and wherein the base surface is perpendicular to the central axis of the assembly and the sensing unit is fixedly mounted thereto.

10. The measuring device of claim 7, constituting an artifact sensor assembly in a measuring device comprising, in addition thereto, at least one biological sensor configured to measure at least one biological parameter.

11. The measuring device of claim 7, wherein the biological sensor faces in the same direction as the contact surface; and wherein the biological sensor is fixed to the contact surface.

12. The measuring device of claim 7, wherein the contact surface constitutes part of a structure, which holds the at least one biological sensor configured for said optical measuring through the contact surface.

13. The measuring device of claim 7, further comprising a control unit in data communication with the detector of the sensor assembly, said control unit comprising
   an analyzer configured to analyze the data received from the detector and generate data indicative of displacement of the contact surface; and
   an output module for communicating said data.

14. The measuring device of claim 7, wherein the biological sensor is one of Electroencephalogram (EEG), Electrocardiography (ECG), photoplethysmograph (PPG), and Galvanic Skin Response (GSR).

15. A measuring device, comprising:
   a displacement sensor assembly configured for use in measuring a biological parameter at the skin of a user, the displacement sensor assembly including:
      a contact surface facing towards an exterior of the assembly for contacting the skin of a user, the contact surface being movable along a central axis of the assembly in response to pressure change at the skin;
      a sensing unit having an optical axis and comprising at least one detector and at least one light source configured to emit light along the optical axis directly towards the detector;
      a light blocking member associated with the sensing unit; and
      a mounting arrangement, by virtue of which the sensing unit and the blocking member are mounted within an interior of the assembly so that one of the sensing unit and the blocking member members is fixedly associated with the contact surface so as to be movable therewith, and the other one is free of such fixed association with the contact surface, the arrangement being such that movement of the member associated with the contact surface relative to the member, which is free of such association, is configured to cause the light blocking member to at least partially block light emitted by the light source towards the detector, allowing that light from the light source received by the light detector to be indicative of the displacement of the contact surface; and
   at least one biological sensor configured for optically measuring at least one biological parameter of a user, the biological sensor is being fixed to the contact surface and facing the same direction as the contact surface for performing the optical measurement via the contact surface.

16. A measuring device, comprising:
   a displacement sensor assembly configured for use in measuring a biological parameter at the skin of a user, the displacement sensor assembly comprises
      a contact surface facing towards an exterior of the assembly and configured for contacting the skin of a user, and movable along a central axis of the assembly in response to pressure change at the skin;
      a sensing unit disposed within an interior of the assembly and having an optical axis lying in a plane perpendicular to the central axis of the assembly; the sensing unit comprises a light source configured to emit light along the optical axis and a light detector facing towards the light source and configured to detect light emitted by the light source directly towards the detector; and
      a light blocking member operative to change the amount of light reaching the detector directly from the light source in consequence with displacement of the contact surface, whereby the light received by the light detector being indicative of the displacement of the contact surface;
   at least one biological sensor fixed to the contact surface and faces in the same direction as the contact surface, the biological sensor is configured for optically measuring at least one biological parameter of a user, the contact surface constituting part of a structure, which hold the at least one biological sensor.

* * * * *